United States Patent
Wang et al.

(10) Patent No.: US 10,461,266 B2
(45) Date of Patent: Oct. 29, 2019

(54) LUMINESCENT COMPOUNDS AND METHODS OF USING SAME

(71) Applicant: Queen's University at Kingston, Kingston (CA)

(72) Inventors: Xiang Wang, Kingston (CA); Suning Wang, Kingston (CA)

(73) Assignee: Queen's University at Kingston, Kingston, ON (CA)

( * ) Notice: Subject to any disclaimer, the term of this patent is extended or adjusted under 35 U.S.C. 154(b) by 204 days.

(21) Appl. No.: 15/622,219

(22) Filed: Jun. 14, 2017

(65) Prior Publication Data

US 2017/0358761 A1 Dec. 14, 2017

Related U.S. Application Data

(60) Provisional application No. 62/349,757, filed on Jun. 14, 2016.

(51) Int. Cl.
| | |
|---|---|
| *H01L 51/50* | (2006.01) |
| *H01L 51/00* | (2006.01) |
| *C07F 15/00* | (2006.01) |
| *C09K 11/06* | (2006.01) |
| *H01L 51/52* | (2006.01) |

(52) U.S. Cl.
CPC ...... *H01L 51/0087* (2013.01); *C07F 15/0086* (2013.01); *C09K 11/06* (2013.01); *C09K 2211/1059* (2013.01); *C09K 2211/185* (2013.01); *H01L 51/5016* (2013.01); *H01L 51/5056* (2013.01); *H01L 51/5072* (2013.01); *H01L 51/5206* (2013.01); *H01L 51/5221* (2013.01); *H01L 2251/533* (2013.01)

(58) Field of Classification Search
None
See application file for complete search history.

(56) References Cited

U.S. PATENT DOCUMENTS

| | | | | |
|---|---|---|---|---|
| 7,655,322 | B2* | 2/2010 | Forrest | C07F 15/0033 257/E51.044 |
| 2006/0134461 | A1* | 6/2006 | Huo | C07F 15/0086 428/690 |
| 2006/0202197 | A1* | 9/2006 | Nakayama | C07F 15/0086 257/40 |
| 2008/0036373 | A1* | 2/2008 | Itoh | C07D 231/12 313/504 |
| 2012/0095232 | A1* | 4/2012 | Li | C07F 15/0086 546/4 |

(Continued)

OTHER PUBLICATIONS

Li, K. et al., "Blue electrophosphorescent organoplatinum(II) complexes with dianionic tetradentate bis(carbene) ligands", Chem. Commun., 2011, 47, 9075-9077.

(Continued)

*Primary Examiner* — Robert S Loewe
(74) *Attorney, Agent, or Firm* — Angela Lyon

(57) ABSTRACT

Compounds are provided that are photoluminescent and electroluminescent, and may emit intense blue or deep blue light. Also provided are methods of producing photoluminescence and electroluminescence, methods of applying the compounds in thin films, and uses of the compounds described herein in a light emitting device, a luminescent probe, a sensor, and/or an electroluminescent device.

20 Claims, 18 Drawing Sheets

(56) References Cited

U.S. PATENT DOCUMENTS

| | | | |
|---|---|---|---|
| 2012/0215001 A1* | 8/2012 | Li | C07F 15/0086 546/4 |
| 2013/0082245 A1* | 4/2013 | Kottas | C07F 15/0086 257/40 |
| 2014/0084261 A1* | 3/2014 | Brooks | C07F 15/0086 257/40 |
| 2016/0028028 A1* | 1/2016 | Li | H01L 51/0087 548/103 |
| 2017/0069855 A1* | 3/2017 | Li | C09K 11/06 |
| 2017/0267923 A1* | 9/2017 | Li | H01L 51/0068 |

OTHER PUBLICATIONS

Unger, Y., et al., "Green-Blue Emitters: NHC-Based Cyclometalalted [Pt(CC)(acac] Complexes", Angew. Chem. Int. Ed., 2010, 49, 10214-10216.

Williams, E.L., et al., "Excimer-Based White Phosphorescent Organic Light Emitting Diodes with Nearly 100% Internal Quantum Efficiency" Advanced Materials, 2007, 19 ,197-202.

Cocchi, M. et al., "Color-variable highly efficient organic electrophosphorescent diodes manipulating molecular exciton and excimer emissions", Applied Physics Letters, 2009, 94, 073309-1-073309-3.

Cocchi, M. et al., "NCN-Coordinated Platinum (II) Complexes as Phosphorescent Emitters in High-Performance Organic Light-Emitting Devices", Advanced Functional Materials, 2007, 17, 285-289.

Yang, X. et al., "Efficient Blue-and White-Emitting Electrophosphorescent Devices Based on Platinum (II) [1,3-Difluoro-4,6-di(2-pyridinyl)benzen] Chloride" Advanced Materials, 2008, 20, 2405-2409.

Chang, S-Y, et al., "Blue-Emitting Platinum(II) Complexes Bearing both Pyridylpyrazolate Chelate and Bridging Pyrazolate Ligands: Synthesis, Structures, and Photophysical Properties" Inorganic Chemistry, 2007, 46, 11202-11212.

Bruce, M.I., "Cyclometalation Reactions", Angewandte Chemie Int'l Ed., 2003,16(2): 73-86.

Brooks, J., et al., "Synthesis and Characterization of Phosphorescent Cyclometalated Platinum Complexes", Inorganic Chemisty, 2002, 41, 3055-3066.

Cockburn, B. N. et al., "Reactivity of Co-ordinated Ligands, Part XV. Formation of Complexes containing Group V Donor Atoms and Metal-Carbon a-bonds", J. Chem. Soc., Dalton Trans. 1973, 404-410.

Sajoto, T. et al., "Temperature Dependence of Blue Phosphorescent Cyclometalated Ir(III) Complexes"J. Am. Chem. Soc., 2009, 131, 9813-9822.

Hudson, Z. et al., "Highly Efficient Blue Phosphorescence from Triarylboron-Functionalized Platinum(II) Complexes of N-Heterocyclic Carbenes", J. Am. Chem. Soc., 2012, 134, 13930-13933.

Li, K., et al., "Light-emitting platinum(II) complexes supported by tetradentate dianionic bis(N-heterocyclic carbene) ligands: towards robust blue electrophosphors", Chem. Sci., 2013, 4, 2630-2644.

Kui, S. C. F., et al., "Robust phosphorescent platinum(II) complexes with tetradentate O^N^C^N ligands high efficiency OLEDs with excellent efficiency stability", Chem. Commun., 2013, 49, 1497-1499.

Cheng, G., et al., "High-Efficiency Polymer Light-Emitting Devices with Robust Phosphorescent Platinum(II) Emitters Containing Tetradentate Dianionic O^N^C^N Ligands", Adv. Mater., 2013, 25, 6765-6770.

Cheng, C., et al., "Structurally robust phosphorescent [Pt(ONCN)] emitters for nigh performance organic light-emitting devices with power efficiency up to 126 Im W-1 and external quantum efficiency over 20%", Chem. Sci., 2014, 5, 4819-4830.

Vezzu, D. A. K., et al., "Highly Luminescent Tetradentate Bis-Cyclometalated Platinum Complexes: Design, Synthesis, Structure, Photophysics, and Electroluminescence Application". Inorg. Chem. 2010, 49, 5107-5119.

Fukagawa, H., et al., "Highly Efficient and Stable Red Phosphorescent Organic Light-Emitting Diodes Using Platinum Complexes", Adv. Mater., 2012, 24, 5099-5103.

Huo, S., et al., "Novel phosphorescent tetradentate bis-cyclometalated CC• NN-coordinated platinum complexes: Structure, photophysics, and a synthetic adventure", Polyhedron, 2013, 52, 1030-1040.

Hang, X.-C., et al., "Highly Efficient Blue-Emitting Cyclornetalated Platinum(II) Complexes by Judicious Molecular Design", Chem. Int. Ed., 2013, 52, 6753-6756.

Fleetham, T., et al., "Efficient "Pure" Blue OLEDs Employing Tetradentate Pt Complexes with a Narrow Spectral Bandwidth", Adv. Mater. 2014, 26, 7116-7121.

Fleetham, T., et al., "Tetradentate Platinum Complexes for Efficient and Stable Excimer-Based White OLEDs", Adv. Funct. Mater. 2014, 24, 6066-6073.

Liao , K.-Y., et al., "Pt(II) Metal Complexes Tailored with a Newly Designed Spiro-Arranged Tetradentate Ligand; Harnessing of Charge-Transfer Phosphorescence and Fabrication of Sky Blue and White OLEDs", Inorg. Chem., 2015, 54, 4029-4038.

Wang , X., et al., "Highly Efficient and Robust Blue Phosphorescent Pt(II) Compounds with a Phenyl-1,2,3-triazolyl and a Pyridyl-1,2,4-triazolyl Chelate Core", Adv. Funct. Mater., 2014, 24, 7257-7271.

Fleetham, T., et al., "Tetradentate Pt(II) Complexes with 6-Membered Chelate Rings: A New Route for Stable and Efficient Blue Organic Light Emitting Diodes", Chemistry of Materials, 2016, 28, 3276-3282.

\* cited by examiner

LUMINESCENT COMPOUNDS AND METHODS OF USING SAME

FIELD

The invention relates to compounds having luminescent (e.g., fluorescent, phosphorescent) properties, and to methods of using such compounds. The invention more particularly relates to compounds having photoluminescent and/or electroluminescent properties, and to uses of same. The invention also relates to compounds having photo-receptor properties due to their ability to separate charges and/or photon harvesting properties.

BACKGROUND

Bright and efficient organic light-emitting diode (OLED) devices and electroluminescent (EL) devices have attracted considerable interest due to their potential application for flat panel displays (e.g., television and computer monitors) and lighting. OLED based displays offer advantages over the traditional liquid crystal displays, such as: wide viewing angle, fast response, lower power consumption, and lower cost. However, several challenges still must be addressed before OLEDs become truly affordable and attractive for next generation display and lighting. To realize white lighting and other full color display applications, it is essential to have the three fundamental colors of red, green, and blue provided by emitters with sufficient color purity and sufficiently high emission efficiency.

Phosphorescent Organic Light-Emitting Diodes (PhOLEDs) have recently received much attention because of their high energy efficiency for next generation flat panel displays and solid state lighting devices. OLEDs based on phosphorescent emitters can have three to four-fold higher device quantum efficiencies than those based on fluorescent emitters. The key challenge in PhOLEDs research is the development of phosphorescent metal complexes with high quantum efficiency and high stability, especially blue phosphorescent compounds. Phosphorescent compounds are among the most sought-after materials by industry around the world as one of the key color components for electroluminescent devices. Blue PhOLEDs based on Pt(II) compounds are rare and only a few examples are known (K. Li, et al., *Chem. Commun.*, 2011, 47, 9075; Y. Unger, et al., *Angew. Chem. Int. Ed.*, 2010, 49, 10214; E. L. Williams et al., *Adv. Mater.* 2007, 19, 197; M. Cocchi, et al., *Appl. Phys. Lett.* 2009, 94, 073309; M. Cocchi, et al., *Adv. Funct. Mater.*, 2007, 17, 285; X. Yang et al., *Adv. Mater.* 2008, 20, 2405; S.-Y. Chang et al., *Inorg. Chem.* 2007, 46, 11202). Up to now, only a few examples of deep blue phosphorescent Pt(II) complexes with Commission internationale de L'Eclairage (CIE) coordinates near deep blue (0.15, 0.15) have been reported in the literature. Hence, there exists a need for blue phosphorescent compounds.

SUMMARY

In an aspect, a compound of general formula (1) is provided;

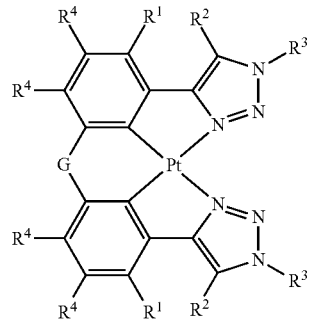

wherein G is oxygen, aliphatic, methylene, carbonyl, amine, silylene, phosphine, phosphine oxide, sulfur, sulfonyl, or a combination thereof; $R^1$ and $R^2$ are independently a hydrogen, an aliphatic moiety (e.g, methyl, $CF_3$) or fluorine, with the proviso that if one of $R^1$ and $R^2$ is aliphatic, $CF_3$, or fluoro (e.g. methyl, $CF_3$, F), then the other is hydrogen; $R^3$ is independently H, or a substituted or unsubstituted aliphatic moiety, substituted or unsubstituted aryl moiety, a substituted or unsubstituted amine, halo, thioether, ether, or any combination thereof, and the $R^3$ of one triazolyl ring can be joined to the $R^3$ of the other triazolyl ring; and $R^4$ is optionally further substituted, and is a non-aromatic carbocycle or heterocycle, an aryl group (which includes a heteroaryl) that is attached as a fused ring or as a substituent, a hydroxy group, nitro, amino, halo, $BR_2$, $B(aryl)_2$, aryl-B(aryl)$_2$, O, $NR_2$, OR, a nitrile group, —C(halo)$_3$, which includes —$CF_3$, and R, where R is a substituted or unsubstituted aliphatic group having 1-24 carbon atoms which may be straight, branched or cyclic (e.g., adamantyl), H, a substituted or unsubstituted aliphatic moiety (e.g., t-butyl, $CF_3$), halo, a substituted or unsubstituted aryl moiety (e.g., phenyl, benzyl), or any combination thereof.

In an embodiment of the above aspect, compounds of general formula (1) are provided having the following structures:

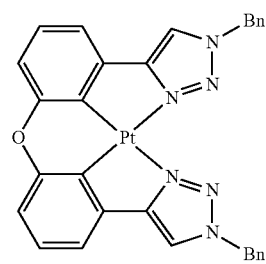

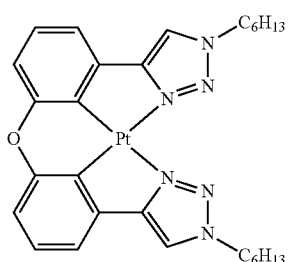

-continued

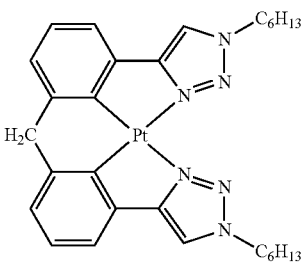

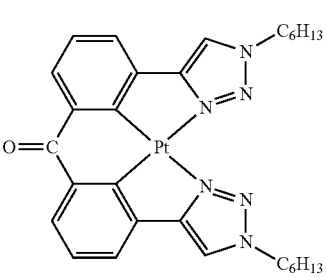

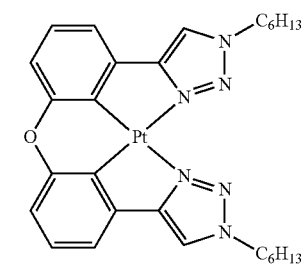

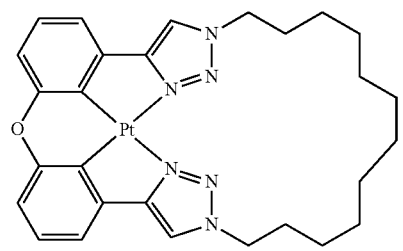

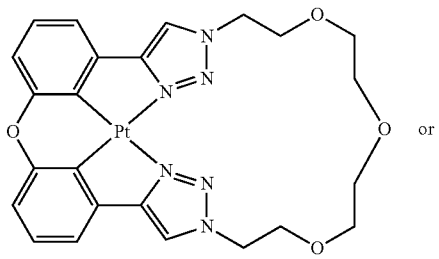 or

-continued

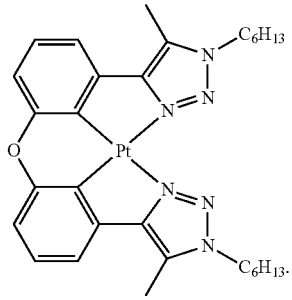
2-Me

In certain embodiments of the above aspect and the above embodiment, the compound is photoluminescent or electroluminescent.

In another aspect, a composition is provided that comprises a photoluminescent or electroluminescent compound as described above, an organic polymer, and a solvent.

In another aspect, a photoluminescent product or an electroluminescent product is provided that comprises a compound as described in the second aspect. In an embodiment of the third aspect, the product is a display device or a lighting device.

In another aspect, a method of producing electroluminescence is provided, that comprises the steps of providing an electroluminescent compound of the first aspect, and applying a voltage across said compound so that said compound electroluminesces.

In another aspect, an electroluminescent device is provided for use with an applied voltage, comprising a first electrode, an emitter which is an electroluminescent compound of the first aspect optionally in a host layer, and a second, transparent electrode, wherein voltage is applied to the two electrodes to produce an electric field across the emitter so that the emitter electroluminesces.

In yet another aspect, an electroluminescent device is provided for use with an applied voltage, comprising a first electrode, a second, transparent electrode, an electron transport layer adjacent the first electrode, a hole transport layer adjacent the second electrode, and an emitter which is an electroluminescent compound as described in the first aspect optionally in a host layer, interposed between the electron transport layer and the hole transport layer, wherein voltage is applied to the two electrodes to produce an electric field across the emitter so that the emitter electroluminesces.

In another aspect, a light emitting device is provided that comprises an anode, a cathode, and an emissive layer, disposed between the anode and the cathode, wherein the emissive layer comprises a compound of general formula (1) of the first aspect. In an embodiment of this aspect, the emissive layer further comprises a host.

In yet another aspect, a consumer product is provided that comprises the device of the preceding aspect.

In another aspect, an electroluminescent device is provided for use with an applied voltage, comprising a first electrode, an emitter which is an electroluminescent compound as described in an embodiment of the first aspect, and a second, transparent electrode, wherein voltage is applied to the two electrodes to produce an electric field across the emitter so that the emitter electroluminesces.

In another aspect, an electroluminescent device is provided for use with an applied voltage, comprising a first electrode, a second, transparent electrode, an electron transport layer adjacent the first electrode, a hole transport layer adjacent the second electrode, and an emitter which is an electroluminescent compound as described in an embodiment of the first aspect interposed between the electron transport layer and the hole transport layer, wherein voltage is applied to the two electrodes to produce an electric field across the emitter so that the emitter electroluminesces.

In yet another aspect, an electroluminescent device is provided for use with an applied voltage, comprising a first electrode, a second, transparent electrode, a layer which is both an emitter and an electron transporter which is an electroluminescent compound as described in an embodiment of the first aspect and which is located adjacent the first electrode, and a hole transport layer which is interposed between the emitter and electron transport layer and the second electrode, wherein voltage is applied to the two electrodes to produce an electric field so that the emitter electroluminesces.

In another aspect, an electroluminescent device is provided for use with an applied voltage, comprising a first electrode, a second, transparent electrode, a layer which is all of an emitter, an electron transporter and a hole transporter which is an electroluminescent compound as described in an embodiment of the first aspect and which is interposed between the first and the second electrode, wherein voltage is applied to the two electrodes to produce an electric field so that the emitter electroluminesces.

In another aspect, an electroluminescent device is provided for use with an applied voltage, comprising a first electrode, a second, transparent electrode, an electron transport layer which is an electroluminescent compound of general formula (1) as described in the first aspect and which is located adjacent the first electrode, a hole transport layer adjacent the second electrode, and an emitter which is interposed between the electron transport layer and the hole transport layer, wherein voltage is applied to the two electrodes to produce an electric field so that the emitter electroluminesces.

In yet another aspect, an electroluminescent device is provided for use with an applied voltage, comprising a first electrode, a second, transparent electrode, an electron transport layer which is located adjacent the first electrode, a hole transport layer which is a compound as described in the first aspect and which is located adjacent the second electrode, and an emitter which is interposed between the electron transport layer and the hole transport layer, wherein voltage is applied to the two electrodes to produce an electric field so that the emitter electroluminesces.

In another aspect an electroluminescent device is provided for use with an applied voltage, comprising a first electrode, a second, transparent electrode, a layer which is both an electron transporter and an emitter which is located adjacent the first electrode, and a hole transport layer which is a compound as described in the first aspect and which is interposed between the electron transport layer and the second electrode, wherein voltage is applied to the two electrodes to produce an electric field so that the emitter electroluminesces.

In yet another aspect an electroluminescent device is provided for use with an applied voltage, comprising a first electrode, a second, transparent electrode, an electron transport layer which is located adjacent the first electrode, and a layer which is both an emitter and a hole transporter which is a compound as described in the first aspect and which is interposed between the electron transport layer and the second electrode, wherein voltage is applied to the two electrodes to produce an electric field so that the emitter electroluminesces.

BRIEF DESCRIPTION OF THE DRAWINGS

For a better understanding of embodiments and to show more clearly how they may be carried into effect, reference will now be made by way of example to the accompanying drawings, which illustrate aspects and features according to preferred embodiments, and in which.

DETAILED DESCRIPTION

Definitions

Figure 1:
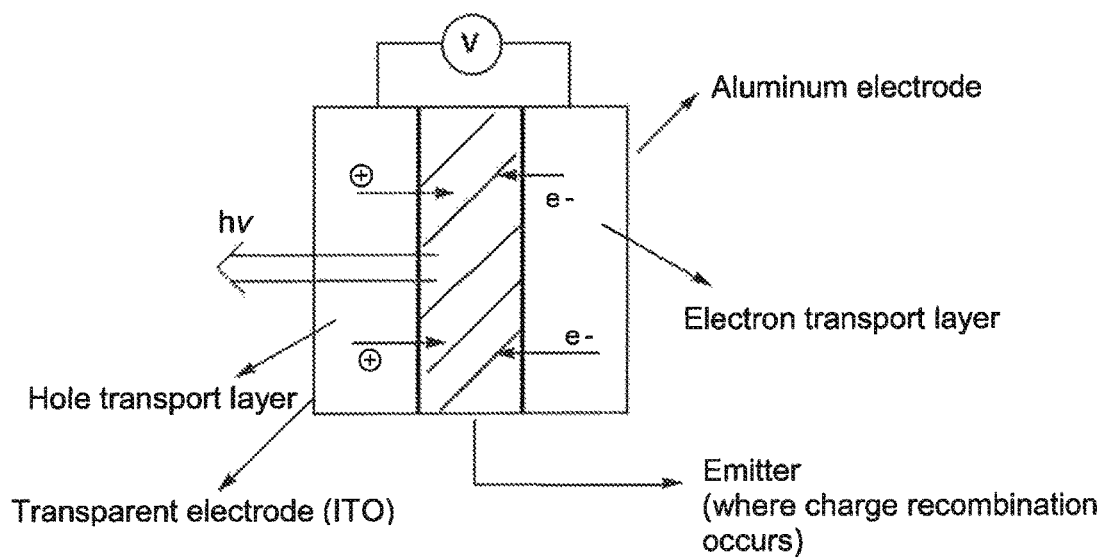
FIG. 1 shows a preferred embodiment of a three layer electroluminescent (EL) display device.

As used herein, the term "TfOH" means trifluoromethanesulfonic acid, which is also known as triflic acid or $CF_3SO_3H$. The term "TsOH" means p-toluenesulfonic acid. The term "TFA" means trifluoroacetic acid. The term "PA" means picolinic acid.

As used herein, the terms "N^C" chelate, "N^N" chelate, "P^C" chelate, and "C^C" chelate are used to indicate what atoms are bonded to the metal. That is, "N^C" indicates that a nitrogen and a carbon are bonded to the metal, "N^N" indicates that two nitrogens are bonded to the metal, "P^C" indicates that a phosphorus and a carbon are bonded to the metal, and "C^C" indicates that two carbons are bonded to the metal.

As used herein, the term "chelation" indicates formation or presence of bonds (or other attractive interactions), e.g., coordination bonds, between a single central atom and two or more separate binding sites within the same ligand.

As used herein, the term "cyclometalation" refers to a reaction of transition metal complexes in which an organic ligand undergoes intramolecular metalation with formation of a metal-carbon sigma bond (Bruce, Michael I., *Angewandte Chemie Int'l Ed.* (2003) 16(2): 73-86).

As used herein "EQE" refers to external quantum efficiency.

As used herein "aliphatic" includes alkyl, alkenyl and alkynyl. An aliphatic group may be substituted or unsubstituted. It may be straight chain, branched chain or cyclic.

As used herein "aryl" includes aromatic carbocycles and aromatic heterocycles and may be substituted or unsubstituted.

As used herein the term "Mes" means mesityl, which is also known as 2,4,6-trimethylphenyl.

As used herein the term "acac" refers to β-diketonato. As used herein the term "nacnac" refers to β-diketimino. As used herein the term picolinato may appear abbreviated as "pico".

As used herein, the term "PMMA" refers to polymethylmethacrylate, a polymer.

As used herein, the term "unsubstituted" refers to any open valence of an atom being occupied by hydrogen. Also, if an occupant of an open valence position on an atom is not specified then it is hydrogen.

As used herein "substituted" refers to the structure having one or more substituents.

As used herein "heteroatom" means a non-carbon, non-hydrogen atom. In some cases, a heteroatom may have a lone pair of electrons available to form dative or coordinate bonds (e.g., N, O, P).

As used herein, the term "dative bond" refers to a coordination bond formed when one molecular species serves as a donor and the other as an acceptor of an electron pair to be shared in formation of a complex.

As used herein, the term "monodentate ligand" refers to a moiety that has a single site that is suitable for binding a metal ion. In general, the stability of a metal complex correlates with the denticity of its ligands, where denticity is defined as, "in a coordination entity the number of donor groups from a given ligand attached to the same central atom" (IUPAC Gold Book). This is thought to be because monodentate ligands are more apt to dissociate from a metal ion than a bidentate or multidentate ligand. This phenomenon is considered to be due to the proximity of the ligand to the metal ion. For example, in solution, when a monodentate ligand dissociates from a metal ion, it drifts away from the metal ion. In contrast, when a bidentate ligand dissociates at one of its two binding sites, the other binding site's bond means that the bidentate ligand remains in the proximity of the metal ion. For this reason, it is likely to reform a bond between the available binding site and the metal ion. Thus a bidentate metal complex is more stable than a monodentate metal complex.

Embodiments

A series of new ligands based on a tetradentate phenyl-1,2,3-triazole core have been prepared and bright blue and deep blue phosphorescent tetradentate Pt(II) compounds based on these ligands have been obtained. These new tetradentate Pt(II) compounds are stable toward UV irradiation and are less prone to excimer formation than other macrocyclic Pt compounds. In addition, as shown in FIGS. 8A, 8B and 9A-N, it has been found that the tetradentate phenyl-1,2,3-triazole macrocyclic Pt(II) molecules have good thermal stability, high phosphorescence quantum efficiency, and undergo little structural change in the excited state, compared to non-macrocyclic tetradentate molecules. Also, bright blue and deep-blue PhOLEDs have been successfully fabricated. Details are presented herein.

Tetradentate N^C^C^N ligands were synthesized as representative examples of chelate chromophores for Pt (II) compounds of general formula (1), which is described herein (see structural formulae in Table 1). The backbones of the ligands were composed of two phenyl-1,2,3-triazolyl units linked by an oxygen atom (L1, L2, L5-L7, L2-Me), a methylene group (L3) or a carbonyl group (L4). For macrocyclic molecules L6 and L7, concentrations of all reagents and catalysts were reduced to one sixth of those for L1-L4 and the reaction time was increased to 6 days. The yields of L6 and L7 (17%-24%) were lower than those of L1-L4 (53%-74%), which is not surprising as the polymerization of the dialkyne and the diazide were competing with the ring closing reaction. In fact, a large quantity of insoluble polymer products precipitated out during the reaction even at the reduced concentration. Further dilution of the solution would result in prolonged reaction time without significant improvement on yield. For L5, due to its asymmetric nature, a different method was used, namely, a Cu(I) catalyzed etherification of aryl halides and phenols. The reaction between the bromine substituted phenyl-triazole and the phenol generated L5 in good yield (77%).

Representative examples of Pt(II) compounds of general formula (1) were prepared using the chelate ligands discussed above (see Table 1). The Pt(II) compounds were obtained in 11-52% yields. All Pt(II) compounds were characterized by NMR, HRMS, and single-crystal X-ray diffraction analyses (for details see Wang, Xiang and Wang, Suning, et al., "Enhancing the stability and phosphorescence efficiency of deep blue phosphorescent Pt(II) complexes with a full steric constraint", under review by Chemical Science, 2016, which is hereby incorporated by reference in its entirety).

The term "cyclometalation" refers to a reaction of a transition metal complex in which an organic ligand undergoes intramolecular metalation with formation of a metal-carbon sigma bond (Bruce, Michael I., *Angewandte Chemie Int'l Ed.* (2003) 16(2): 73-86). Cyclometallated Pt complexes of general formula (1), as described below, have promising PhOLED properties such as high photoluminescent quantum efficiencies and may offer one or more of the key color components for electroluminescent devices. Details regarding synthesis and characterization of such compounds are provided herein. Compounds having general formula (1) are:

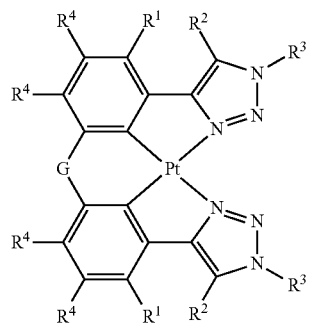

(1)

wherein G is oxygen, methylene, carbonyl, amine, silylene, phosphine, phosphine oxide, sulfur, or sulfonyl, $R^1$, and $R^2$ are independently a hydrogen, alkyl (e.g., $CH_3$), $CF_3$, or fluorine, provided that there is little to no steric interaction between them, so, if one of $R^1$ and $R^2$ is an alkyl (e.g. methyl, $CF_3$) or F, then the other is hydrogen, $R^3$ is H, or a substituted or unsubstituted aliphatic moiety, substituted or unsubstituted aryl moiety or any combination thereof, or a substituted or unsubstituted amine, halo, thioether, ether, or any combination thereof, and the $R^3$ of one triazolyl ring can be joined to the $R^3$ of the other triazolyl ring, and $R^4$ can be any chemical moiety that does not interfere with the desired reaction and may be further substituted, it may include, for example: a non-aromatic carbocycle or heterocycle, an aryl group (which includes a heteroaryl) that is attached as a fused ring or as a substituent, a hydroxy group, nitro, amino, halo, $BR_2$, $B(aryl)_2$, aryl-$B(aryl)_2$, O, $NR_2$, OR, a nitrile group, $—C(halo)_3$ which includes $—CF_3$, and R, where R is a substituted or unsubstituted aliphatic group having 1-24 carbon atoms which may be straight, branched or cyclic (e.g., adamantyl), H, a substituted or unsubstituted aliphatic moiety (e.g., t-butyl, $CF_3$), halo, a substituted or unsubstituted aryl moiety (e.g., phenyl, benzyl), or any combination thereof.

In certain embodiments of general formula (1), compounds have a structure of general formula (1A):

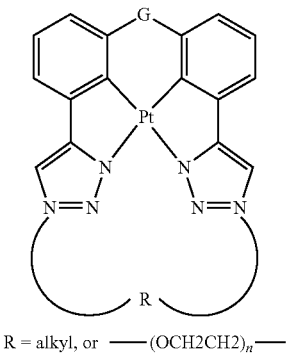

(1A)

R = alkyl, or ——$(OCH2CH2)_n$—— where G is as defined above. Examples of such compounds include 6 and 7 (see Table 1 for structural formulae).

When the substituted cyclometalating ligand is used to form a compound of general formula (1), a highly efficient phosphorescent Pt(II) compound can be achieved. In some embodiments, the phosphorescence is blue. In certain embodiments the phosphorescence is deep blue.

The effect of the presence of substituents plays an important role in the high performance of the resulting Pt(II) compounds of general formula (1) in PhOLEDs. It facilitates the mixing of the $^3$LC and the MLCT state, thus enhancing the intrinsic phosphorescent efficiency of the molecule. It minimizes intermolecular interactions, thus enhancing emission efficiency in the solid state. Also, it also enhances the rigidity of the molecule, thus minimizing the loss of phosphorescence via non-radiative pathways. In certain embodiments, a compound of general formula (1) exhibits intense luminescence, which may be photoluminescence and/or electroluminescence.

Compounds of general formula (1) comprise two 1,2,3-triazolyl moieties that are bonded to the Pt through a nitrogen ring atoms. That is, two aromatic 5-membered heterocycles that each have three ring nitrogens located all in a row. The triazolyl rings may be independently substituted or unsubstituted. In some embodiments, the phenyl rings are unsubstituted. Substituents may include, independently, H, a substituted or unsubstituted aliphatic moiety, a substituted or unsubstituted aryl moiety, a substituted or unsubstituted amine, halo, thioether, ether, or any combination thereof. Some embodiments have a substituent located at the 3-nitrogen position of the triazolyl moiety; such nitrogen substituents may include benzyl, $C_6H_{13}$, aliphatic (e.g., methyl), aryl, $C_{12}H_{24}$, or $C_8O_3H_{16}$. Suitable substituents include any moiety that does not interfere with the luminescence of such compounds. Optionally, the triazolyl rings may be connected to one another through a hydrocarbon chain, or through a carbon, hydrogen and oxygen chain (see formula (1A) and 6 and 7).

The cyclometalating ligand formed by one phenyl ring and one triazolyl ring of general formula (1) is a bidentate ligand, and as such, two atoms form bonds with the Pt(II). The first metal-bonding atom is a carbon ring atom of the phenyl ring, and the second is a nitrogen ring atom of the triazolyl ring. This bidentate ligand is referred to herein as a phenyl-triazolyl ligand. This bidentate ligand is stabilizing because it saturates the coordination sphere of the Pt(II) center and provides a rigidity to the molecule, which discourages ligands from dissociating from the Pt(II).

Prior to this discovery, cyclometalated platinum β-diketonates have typically been prepared by a modified method of Lewis and coworkers (Brooks, J. et al. *Inorg. Chem.* 2002, 41, 3055-3066; and Cockburn, B. N. et al. *J. Chem. Soc., Dalton Trans.* 1973, 404-410). This process is a two-step process in which 2 to 2.5 equivalents of cyclometalating ligand are heated with $K_2PtCl_4$ to give a chloro-bridged platinum dimer, which is then heated with $Na_2CO_3$ and β-diketone to give the final product.

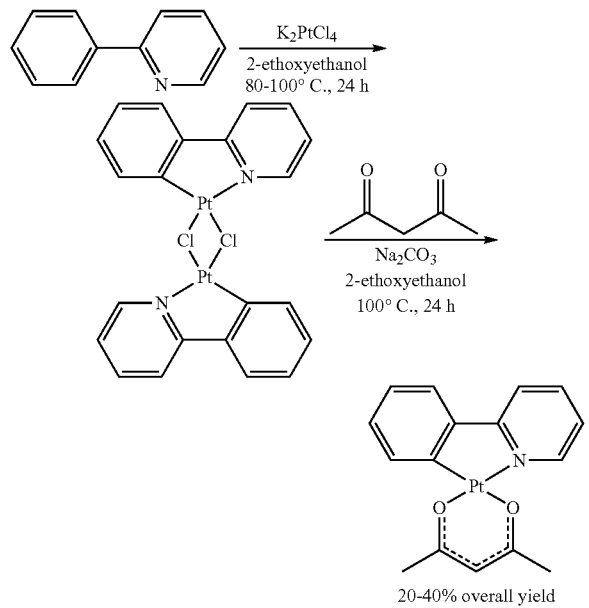

This previously known process has several disadvantages. It requires long reaction times at high temperatures and provides typical yields of only 20-40% over two steps. Its requirement for excess ligand can be particularly problematic, as the organic ligands used for many applications in advanced materials are often of considerable value. Furthermore, high temperature reaction conditions limit the variety of cyclometalating ligands that can be used to prepare such complexes.

The working examples provide detailed descriptions of syntheses of specific compounds of general formula (1), whose structural formulae are shown in Table 1. As would be apparent to a person of ordinary skill in the art, other structural variations may be used. Starting materials may be modified to include moieties that confer desirable physical or chemical properties, such as increased stability or luminescence.

A series of new blue, deep blue and blue-green phosphorescent compounds have been described herein. Substituent groups on the ligands were found to influence the extent of excimer formation and quantum efficiency. Synthetic details are provided in the Working Examples. Data regarding luminescence of compounds of general formula (1) is shown in the Tables and Figures. Such compounds of general formula (1) are photoluminescent or electroluminescent. Thus, embodiments provide compounds that are photoluminescent and, in at least some embodiments, electroluminescent; they may produce intense light.

In one embodiment, a composition is provided which comprises a photoluminescent or electroluminescent compound of general formula (1), an organic polymer, and a solvent. In other embodiments, a composition is provided which comprises a photoluminescent or electroluminescent compound of general formula (1), an organic polymer, and a solvent.

In one embodiment, a method of producing photoluminescence is provided that comprises the steps of: providing a photoluminescent compound having general formula (1); and irradiating said photoluminescent compound with radiation of a wavelength suitable for exciting the compound to photoluminesce.

In one embodiment, a method of producing electroluminescence is provided that comprises the steps of: providing an electroluminescent compound having general formula (1); and applying a voltage across said electroluminescent compound.

In one embodiment, an electroluminescent device is provided for use with an applied voltage, that comprises a first electrode, an emitter (e.g., phosphor) which is an electroluminescent compound optionally doped in a host material, and a second, transparent electrode, wherein a voltage is applied between the two electrodes to produce an electric field across the emitter.

In one embodiment, an electroluminescent device is provided for use with an applied voltage, comprising: a first electrode, an electron transport layer, an emitter (e.g., phosphor) which is an electroluminescent compound doped in a host material, a hole transport material, and a second, transparent electrode. When a voltage is applied between the two electrodes, it produces an electric field across the emitter and the emitter consequently electroluminesces. In some embodiments, the device includes one or more charge transport layers interposed between the emitter and one or both of the electrodes. For example, as shown in FIG. 1, spacing of an embodiment of the device, called for the purposes of the present specification, a "three layer EL device", is: first electrode, first charge transport layer, emitter in a host layer, second charge transport layer, and second transparent electrode.

In certain embodiments, compounds of general formula (1) are soluble in common solvents such as hexane, toluene, diethyl ether, tetrahydrofuran (THF), dichloromethane and alcohols. This permits the compounds to be blended easily and conveniently with polymers. The role of the polymer in such a mixture is at least two-fold. First, a polymer can provide protection for the compound from air degradation. Second, a polymer host matrix permits use of a solution-based process (e.g., ink-jet printing), a spin-coating process, or a dip-coating process as an alternative way to make films. Although spin-coating and dip-coating processes may not produce as high quality films as those produced by chemical vapor deposition (e.g., ink-jet printing) or vacuum deposition, they are often much faster and more economical.

Accordingly, one embodiment further provides methods of applying compounds as described above to a surface. These methods include solvent cast from solution, electrochemical deposition, vacuum vapor deposition, chemical vapor deposition, spin coating and dip coating. The compounds may be applied alone or with a carrier. In some embodiments, they are applied in a composition including an organic polymer. Such compositions are also encompassed by an embodiment of the invention. As an example of this application, compounds of general formula (1) form a clear transparent solution with the weakly-luminescent polymer PMMA. This can be converted to a transparent film by evaporating the toluene solvent via either a dip-coating or spin-coating process. Films obtained in this way are stable. Certain polymers such as, for example, PVK, are expected to further enhance the luminescence of an emitter in the film.

Conveniently, spin coating may be performed using a Chemat Technology spin-coater KW-4A; and vacuum deposition may be performed using a modified Edwards manual diffusion pump.

Certain compounds of general formula (1) have high chemical and/or thermal stability. See thermal stability data in Figures (8A and B) for a representative example. As a result of their high stability, they are suitable for vacuum deposition methods used in fabricating single- or multi-layer OLED devices.

In one embodiment, a method of producing electroluminescence is provided that comprises the steps of: providing an electroluminescent compound having general formula (1); and applying a voltage across said electroluminescent compound so that the compound electroluminesces.

According to one embodiment, electroluminescent devices for use with an applied voltage are provided. In general, such a device has a first electrode, an emitter which is an electroluminescent compound, and a second, transparent electrode, wherein a voltage is applied between the two electrodes to produce an electric field across the emitter of sufficient strength to cause the emitter to electroluminesce. Preferably, the first electrode is of a metal, such as, for example, aluminum, which reflects light emitted by the compound; whereas the second, transparent electrode permits passage of emitted light therethrough. The transparent electrode is preferably of indium tin oxide (ITO) glass, flexible polymer, or an equivalent known in the art. Here, the first electrode is the cathode and the second electrode is the anode.

In some embodiments, an EL device includes one or more charge transport layers interposed between the emitter and one or both of the electrodes. Such charge transport layer(s) are employed in prior art systems with inorganic salt emitters to reduce the voltage drop across the emitter. In a first example of such a device, layers are arranged in a sandwich in the following order: first electrode, charge transport layer, emitter and host, second charge transport layer, and second transparent electrode. In an embodiment of this type, a substrate of glass, quartz or the like is employed. A reflective metal layer (corresponding to the first electrode) is deposited on one side of the substrate, and an insulating charge transport layer is deposited on the other side. The emitter layer which is a compound of general formula (1) is deposited on the charge transport layer, preferably by vacuum vapor deposition, though other methods may be equally effective. A transparent conducting electrode (e.g., ITO) is then deposited on the emitter layer. An effective voltage is applied to produce electroluminescence of the emitter.

In a second example of an EL device, a second charge transport layer is employed, and the sandwich layers are arranged in the following order: first electrode, first charge transport layer, emitter and host, second charge transport layer and second, transparent electrode.

Electroluminescent devices may include one or more of the emitting compounds described herein. In some embodiments, an electroluminescent device such as a display device (e.g., flat panel display device, flexible display device, wearable display device) may include not only a blue-, deep blue- or green-emitting phosphor as described herein, but may be a multiple-color display device including one or more other phosphors. The other phosphors may emit in other light ranges, e.g., red, green, and/or be "stacked" relative to each other. Convenient materials, structures and uses of electroluminescent display devices are described in Rack, P. D.; Naman, A.; Holloway, P. H.; Sun, S.-S.; and Tuenge, R. T. Materials used in electroluminescent displays." *MRS Bulletin* (1996) 21(3): 49-58.

For photoluminescence, the compounds absorb energy from ultraviolet radiation and emit visible light near the ultraviolet end of the visible spectrum, e.g., in the blue region. For electroluminescence, the absorbed energy is from an applied electric field.

One embodiment further provides methods employing compounds described herein to harvest photons, and corresponding devices for such use. Spectroscopic studies have demonstrated that such compounds have high efficiency to harvest photons and produce highly polarized electronic transitions. In general, when such compounds are excited by light, a charge separation occurs within the molecule; a first portion of the molecule has a negative charge and a second portion has a positive charge. Thus the first portion acts as an electron donor and the second portion as an electron acceptor. If recombination of the charge separation occurs, a photon is produced and luminescence is observed. In photovoltaic devices, recombination of the charge separation does not occur; instead the charges move toward an anode and a cathode to produce a potential difference, from which current can be produced.

Organic semiconducting materials can be used in the manufacture of photovoltaic cells that harvest light by photo-induced charge separation. To realize an efficient photovoltaic device, a large interfacial area at which effective dissociation of excitons occurs must be created; thus an electron donor material is mixed with an electron acceptor material. (Here, an exciton is a mobile combination of an electron and a hole in an excited crystal, e.g., a semiconductor.) Luminescent compounds as semiconductors are advantageous due to their long lifetime, efficiency, low operating voltage and low cost.

The molecular design of compounds of general formula (1) was intended to achieve high-energy blue phosphorescence with maximum quantum yield ($\phi_P$). The C^N chelate backbone of the phenyl-triazolyl ligand presents a strong ligand field to the Pt(II) centre, raising the energy of non-radiative d-d excited states and reducing thermal quenching. The stabilizing ring provides good solubility as well as solution- and solid-state stability, while its rigid structure and high triplet energy level help to increase $\phi_P$.

As show in Tables herein, doped PMMA films (5 or 10 wt %, as indicated) of Pt(II) complexes of general formula (1) exhibited good quantum yields. Such complexes displayed bright phosphorescence with emission colors ranging from deep blue to blue-green.

Embodiments further provide methods of applying described compounds to a surface. These methods include solvent cast from solution, electrochemical deposition, vacuum vapor deposition, chemical vapor deposition, spin coating and dip coating. The compounds may be applied alone or with a carrier. In some embodiments, they are applied in a composition including an organic polymer. Such compositions are also encompassed by certain embodiments. As an example of this application, compounds of general formula (1) form a clear transparent solution with the weakly-luminescent polymer PMMA. This can be converted to a transparent film by evaporating the toluene solvent via either a dip-coating or spin-coating process. Films obtained in this way are stable. Certain polymers such as, for example, PVK, are expected to further enhance the luminescence of an emitter in the film. Conveniently, spin coating may be performed using a Chemat Technology spin-coater KW-4A; and vacuum deposition may be performed using a modified Edwards manual diffusion pump.

Certain compounds of general formula (1) have high chemical and/or thermal stability. As a result, they are suitable for vacuum deposition methods used in fabricating single- or multi-layer OLED devices.

In one embodiment a method of producing electroluminescence is provided that comprises the steps of: providing an electroluminescent compound having general formula (1); and applying a voltage across said electroluminescent compound so that the compound electroluminesces.

Based on the excellent phosphorescent quantum efficiency, the deep blue emission colour and the good thermal stability, 6 was selected to test its performance in electroluminescence devices. EL devices with device structures of Glass/ITO/NPB (60 nm)/mCP (10 nm)/BCPO:6 x % (200 nm)/DPEPO (10 nm)/TPBi (300 nm)/LiF (1 nm)/Al (100 nm) are fabricated. N,N'-Di(1-naphthyl)-N,N'-diphenyl-(1,1'-biphenyl)-4,4'-diamine (NPB) and 1,3,5-Tris(1-phenyl-1H-benzimidazol-2-yl)benzene (TPBi) were chosen as hole injection material and electron injection layer, respectively. The electron transport material bis[2-(diphenylphosphino) phenyl] ether oxide (DPEPO) and the hole transport material 1,3-Bis(N-carbazolyl)benzene (mCP) were selected because of their high triplet energy (3.00 eV and 2.90 eV, respectively). The host material 9,9'-(4,4'-(Phenylphosphoryl)bis-(4,1-phenylene))bis (9H-carbazole) (BCPO) was used because of its high triplet energy (3.01 eV) and its bipolar nature which facilitates conduction of both electrons and holes. The energy diagram (FIG. 2) and molecular structures of the materials (Table 1) used in the devices are shown herein. Doping concentrations were at 2%, 5% and 10% and the data are shown in Tables 3 and 4, and FIGS. 6A-C. In all three devices, deep blue emission with $\lambda$=452 nm and CIEx+y less than 0.3 have been achieved. It can be seen that the emission spectra at the three doping levels remain almost the same, except a small increase of the peak at around 510 nm. Device with 10% 6 shows the best performance, with maximum current efficiency, power efficiency and external quantum efficiency of 11.0 cd/A, 10.8 lm/W and 9.7%, which remain at 8.5 cd/A, 3.3 lm/W and 7.5% at 1000 cd/m$^2$. Notably, the devices were not sealed and all measurements were performed under air, which could greatly facilitate the decomposition of various materials in the EL device. Further work is being carried out on optimizing the device structure and testing the performance under inert conditions.

Molecules with the ability to separate charges upon light initiation are useful for applications such as photocopiers, photovoltaic devices and photoreceptors. Photoconductors provided by compounds of general formula (1) are expected to be useful in such applications, due to their stability and ability to be spread into thin films. Related methods are encompassed herein.

Photocopiers use a light-initiated charge separation to attract positively-charged molecules of toner powder onto a drum that is negatively charged.

Referring to FIG. 1, an embodiment of an electroluminescent device is shown. In general, when a potential is applied across an OLED, holes are said to be injected from an anode into a hole transporting layer (HTL) while electrons are injected from a cathode into an electron transporting layer (ETL). The holes and electrons migrate to an ETL/HTL interface. Materials for these transporting layers are chosen so that holes are preferentially transported by the HTL, and electrons are preferentially transported by the ETL. At the ETL/HTL interface, the holes and electrons recombine to give excited molecules which radiatively relax, producing an EL emission that can range from blue to near-infrared (Koene, B.; Loy, D.; and Thompson, M. Unsymmetrical Triaryldiamines as Thermally Stable Hole Transporting Layers for Organic Light-Emitting Devices. *Chemistry of Materials.* (1998) 10(8): 2235-2250).

Figure 2:
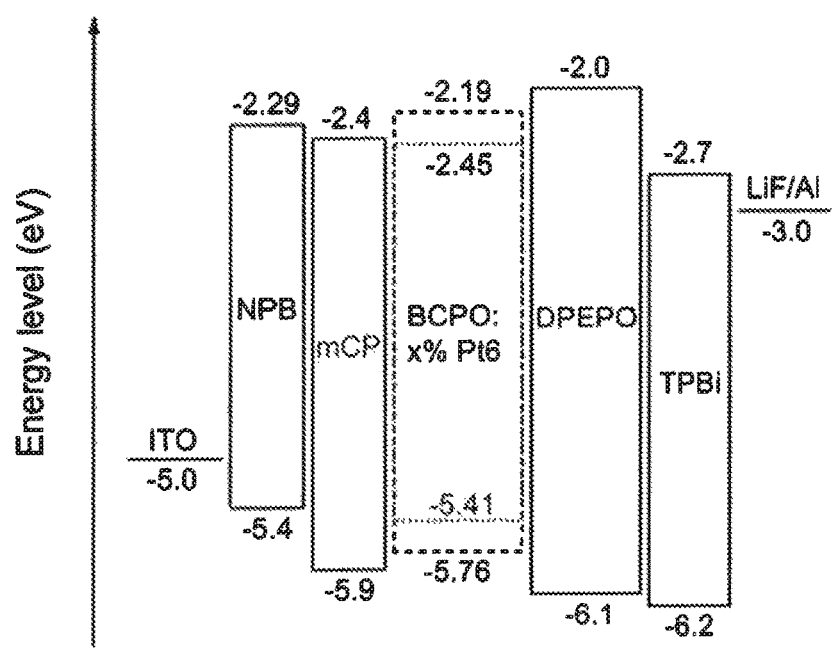
FIG. 2 shows an energy digram of various materials used in EL devices.
Figure 3:
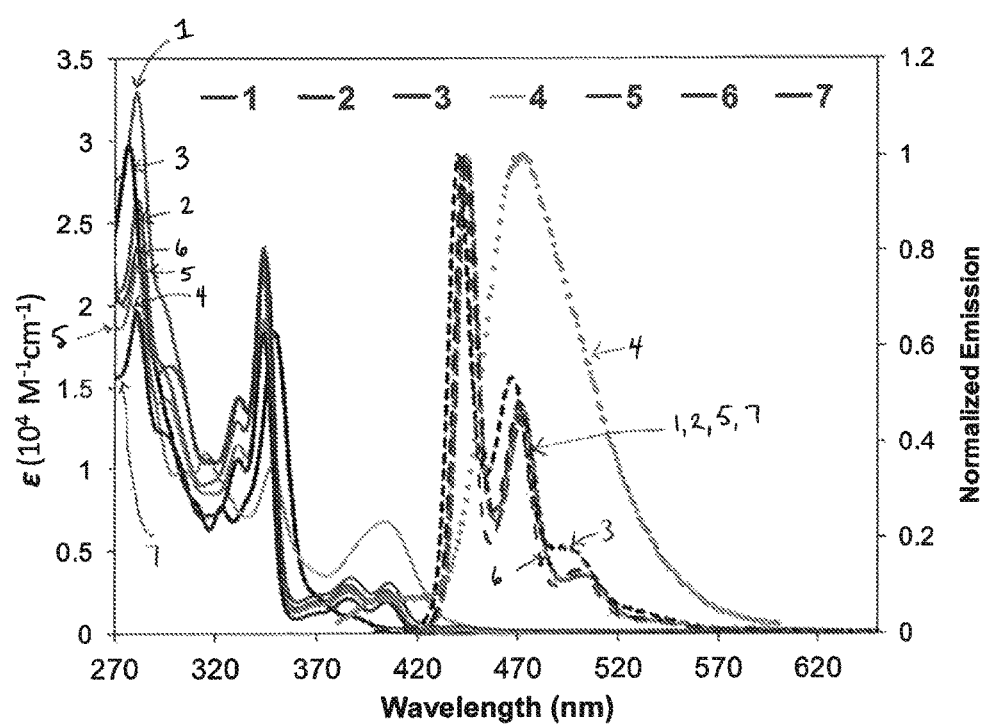
FIG. 3 shows absorption (solid lines) and phosphorescent (dashed lines) spectra of Pt(II) compounds in $CH_2Cl_2$ at ambient temperature.
Figure 4:
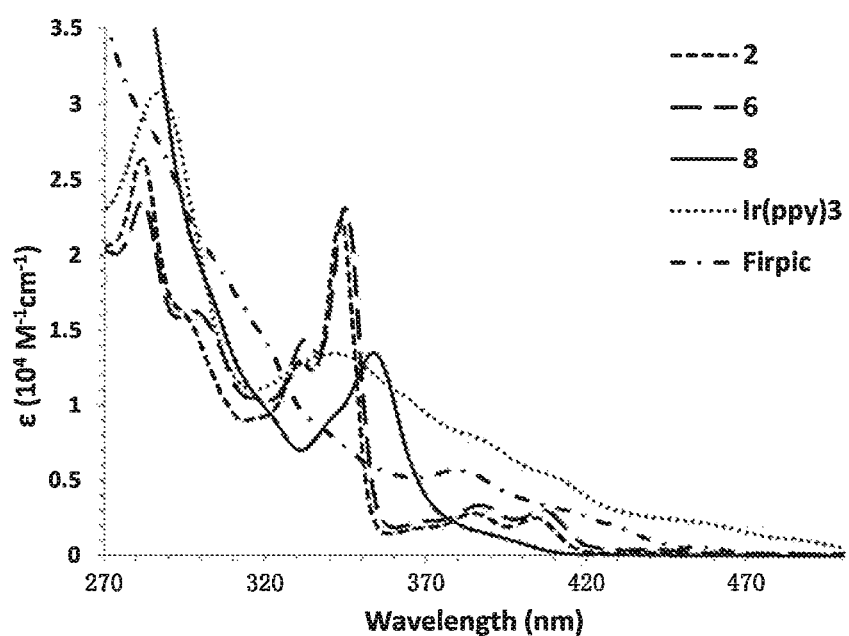
FIG. 4 shows absorption spectra of 2, 6, 8, Ir(ppy)$_3$ and Firpic in $CH_2Cl_2$ (~$2\times10^{-5}$M) at ambient temperature
Figure 5A:
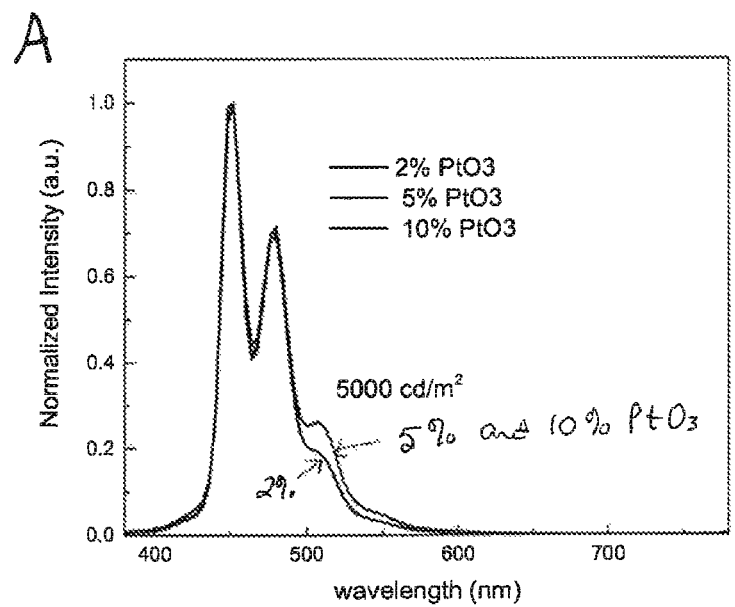
FIG. 5A shows an EL spectra of EL devices based on 6.
Figure 5B:
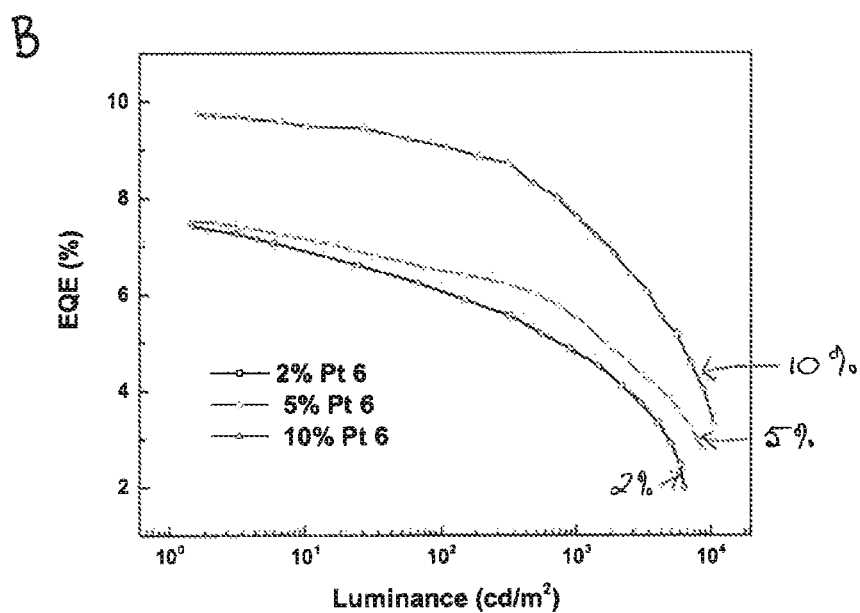
FIG. 5B shows an EQE-L plot of EL devices based on 6.
Figures 6A, 6B, 6C:
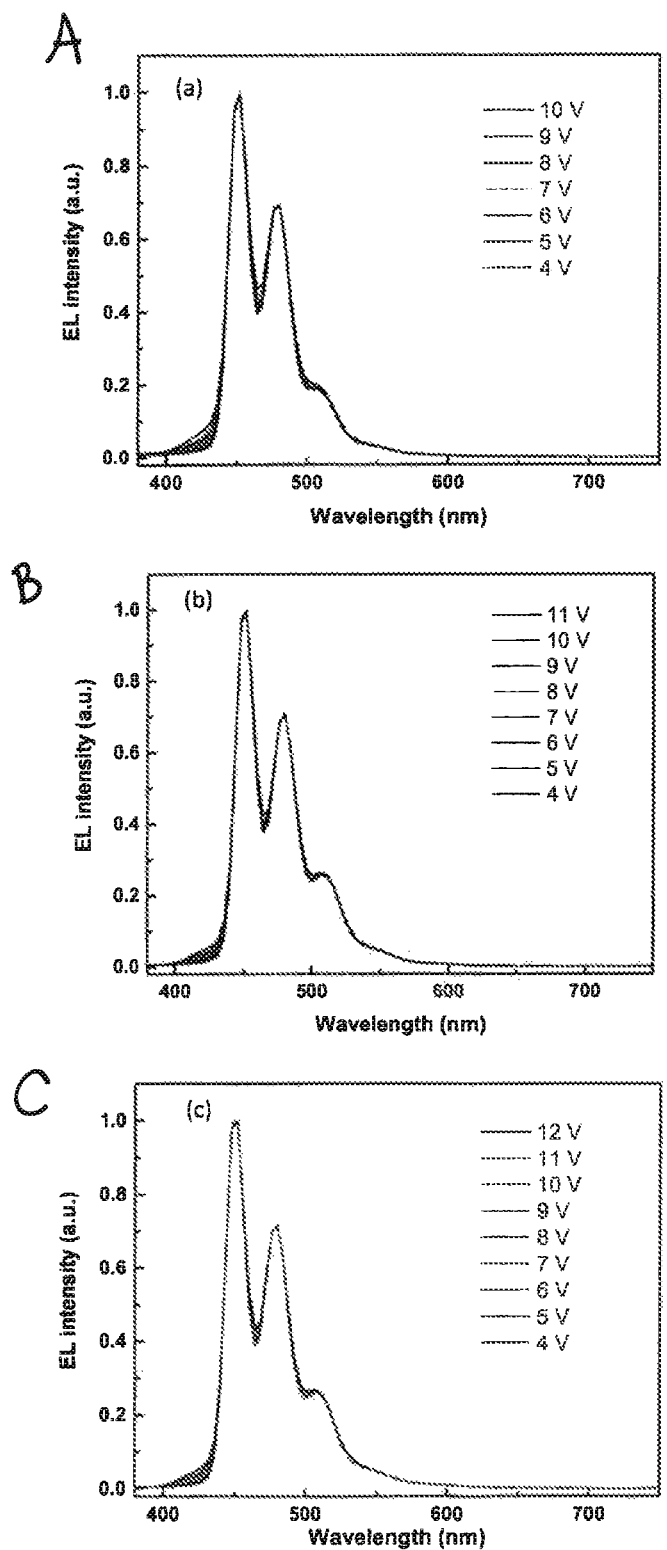
FIGS. 6A-C show L-V curves of EL devices based on 6, (A) 2% of 6 doped in BCPO as emitter; (B) 5% of 6 doped in BCPO as emitter; and (C) 10% of 6 doped in BCPO as emitter.
Figures 7A, 7B, 7C:
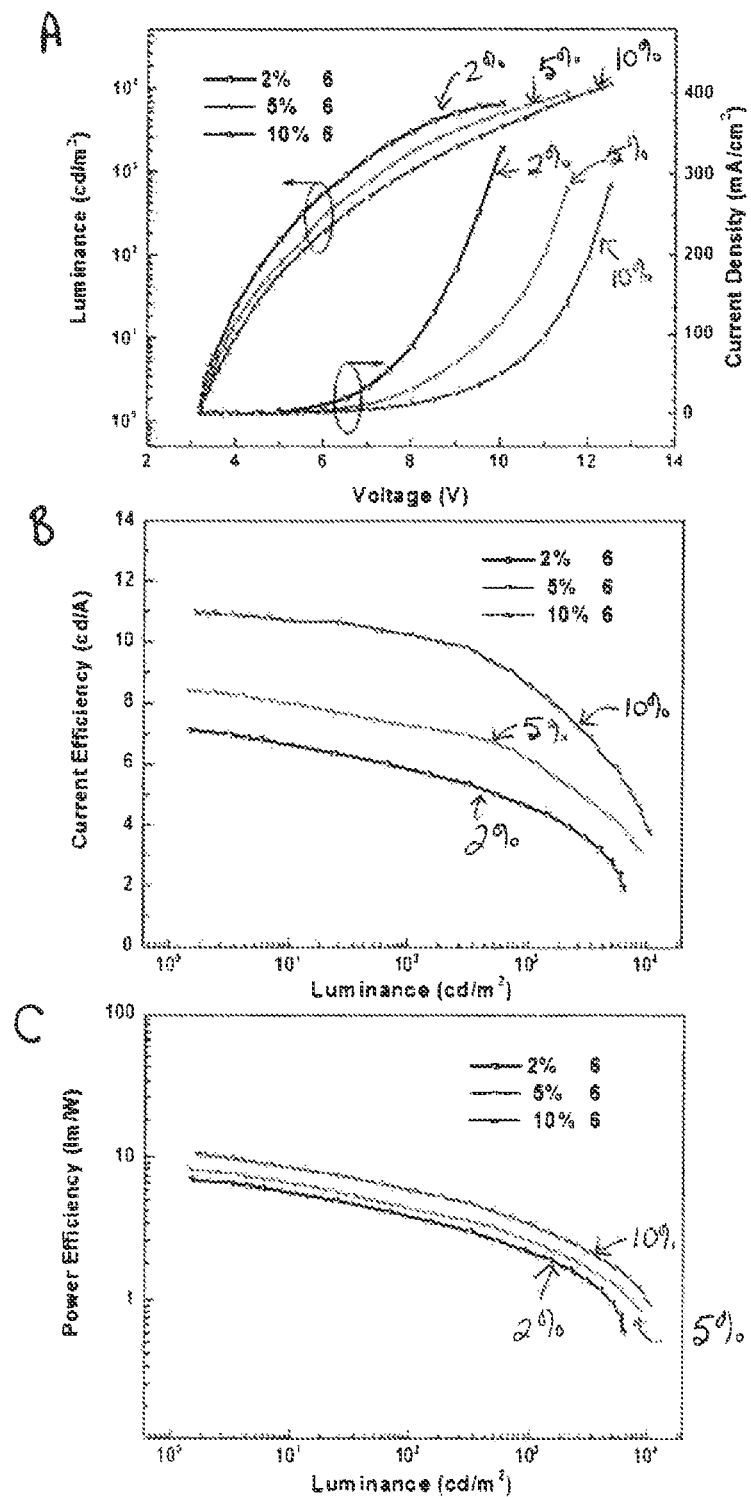
FIGS. 7A-C show L-J-V and current efficiency and power efficiency diagrams of EL devices based on 6.
Figures 8A, 8B:
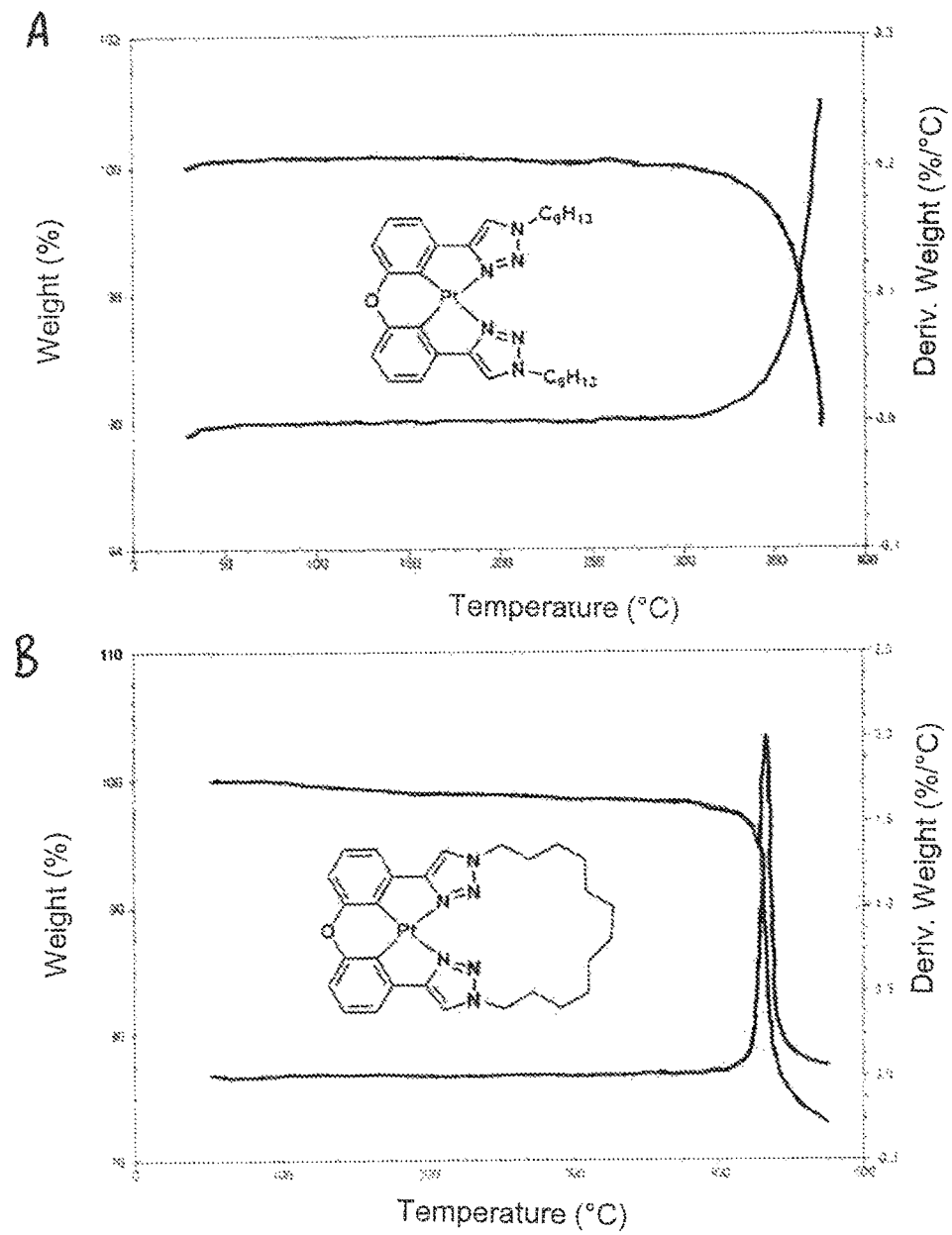
FIG. 8A shows a thermogravimetric analysis (TGA) diagram of 2, recorded under nitrogen.
FIG. 8B shows a thermogravimetric analysis (TGA) diagram of 6, recorded under nitrogen.
Figure 9A:
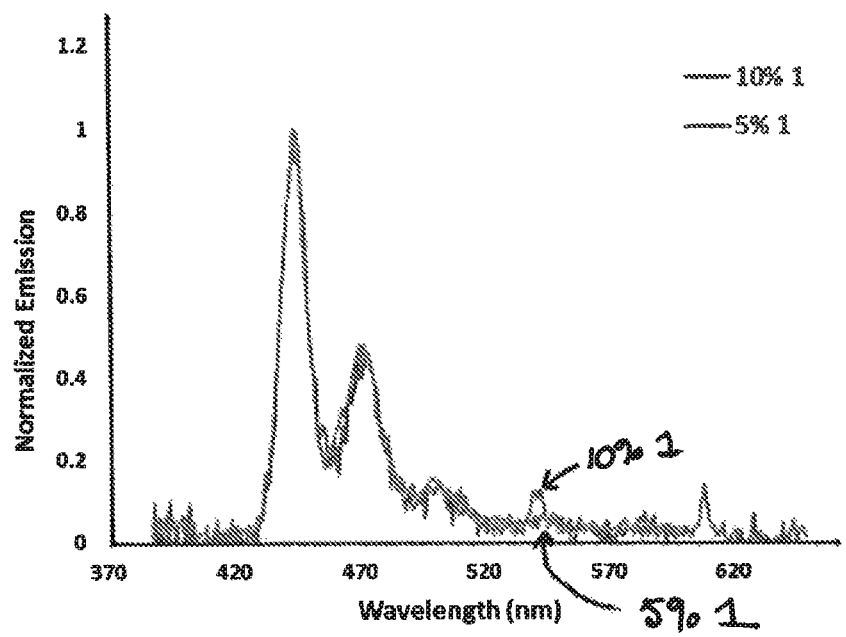
FIG. 9A shows a phosphorescent emission spectra of 1 in doped PMMA films.
Figure 9B:
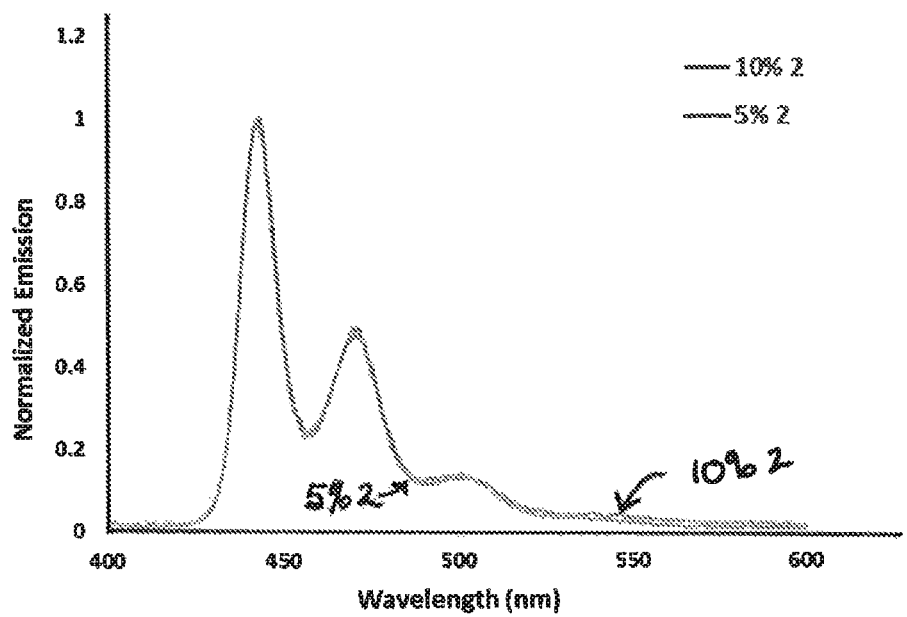
FIG. 9B shows a phosphorescent emission spectra of 2 in doped PMMA films.
Figure 9C:
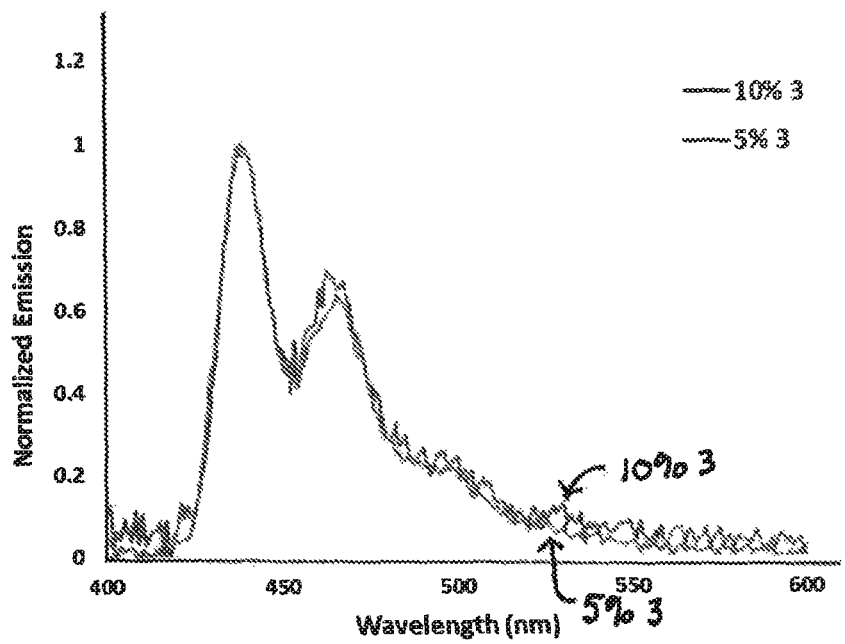
FIG. 9C shows a phosphorescent emission spectra of 3 in doped PMMA films.
Figure 9D:
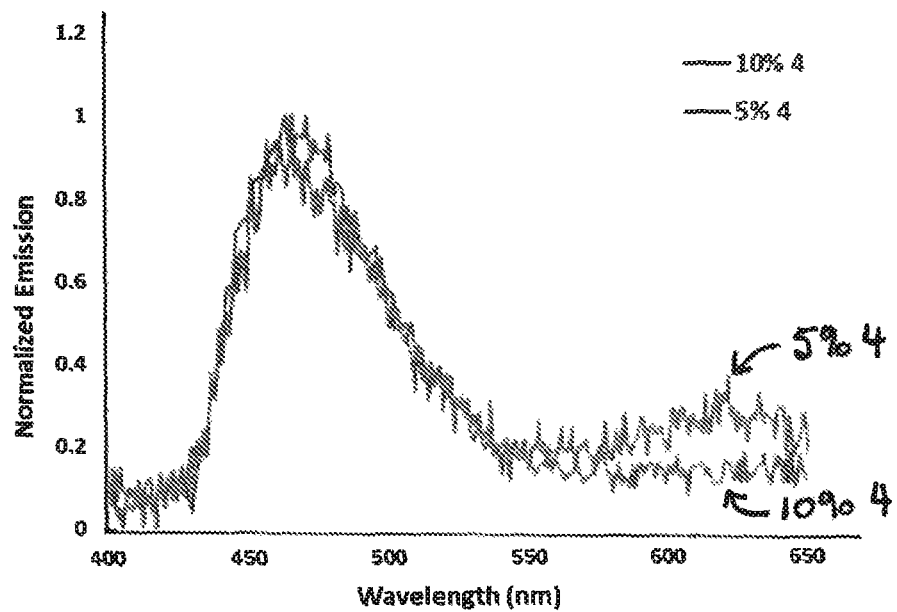
FIG. 9D shows a phosphorescent emission spectra of 4 in doped PMMA films.
Figure 9E:
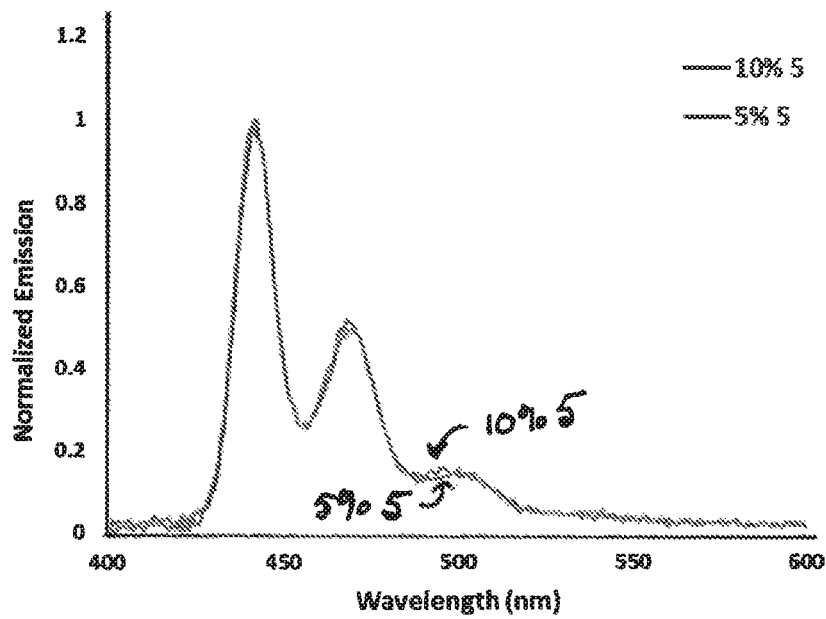
FIG. 9E shows a phosphorescent emission spectra of 5 in doped PMMA films.
Figure 9F:
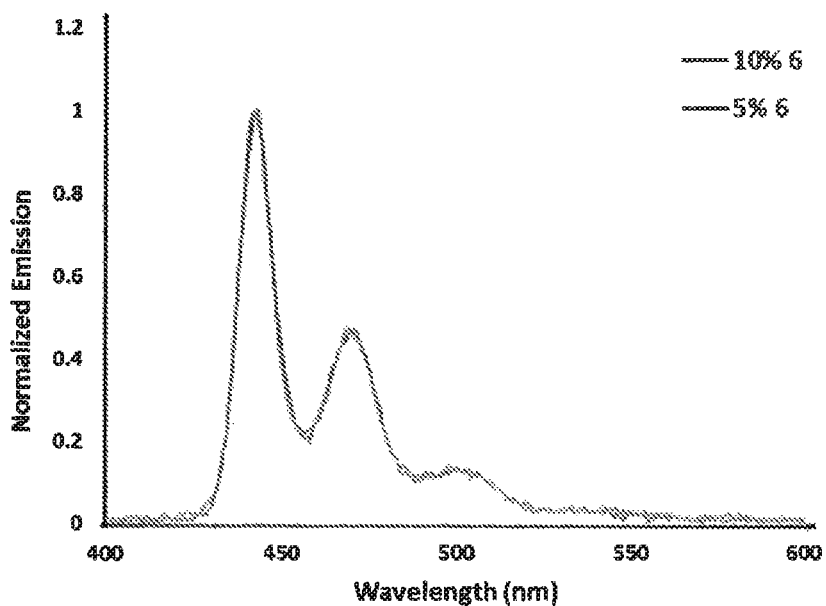
FIG. 9F shows a phosphorescent emission spectra of 6 in doped PMMA films.
Figure 9G:
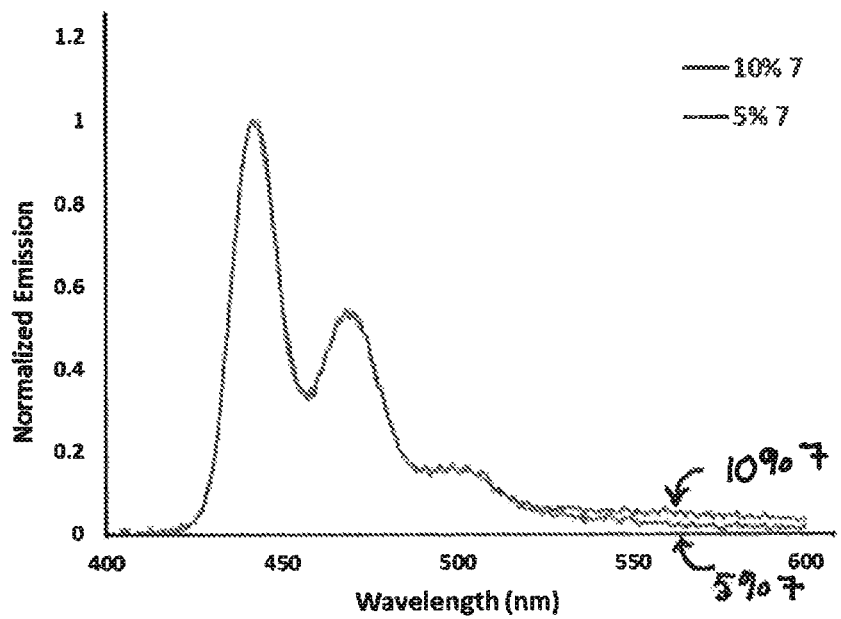
FIG. 9G shows a phosphorescent emission spectra of 7 in doped PMMA films.
Figure 9H:
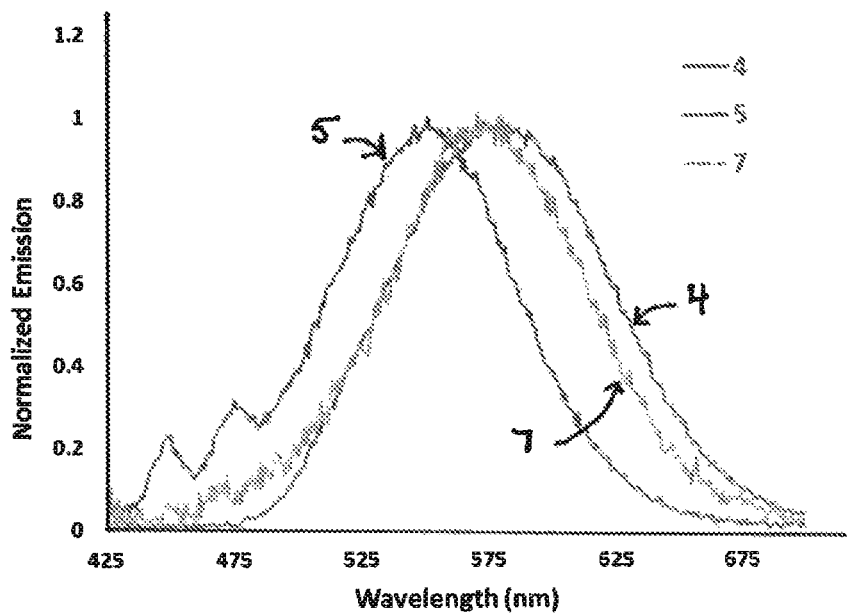
FIG. 9H shows a phosphorescent emission spectra of 4, 5 and 7 as neat powder.
Figure 9I:
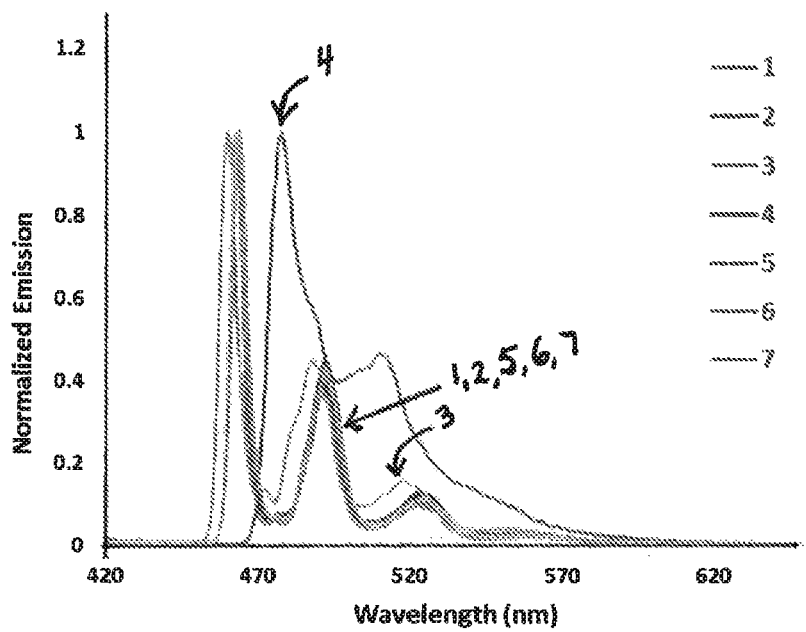
FIG. 9I shows a phosphorescent emission spectra of compounds 1-7 (~$2\times10^{-5}$ M in 2-methyl THF) at 77K.
Figure 9J:
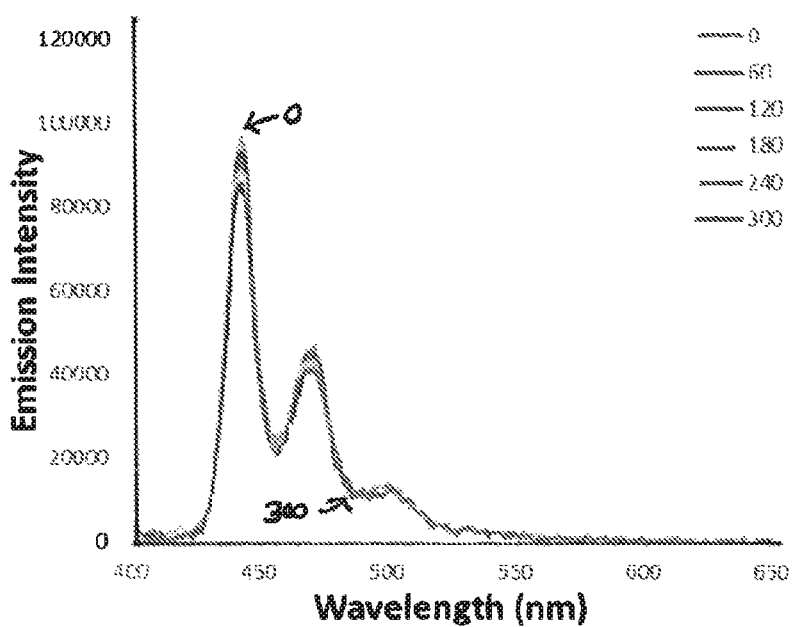
FIG. 9J shows a phosphorescent emission spectra of 2 in doped PMMA films under continuous UV irradiation (350 nm, 300 minutes).
Figure 9K:
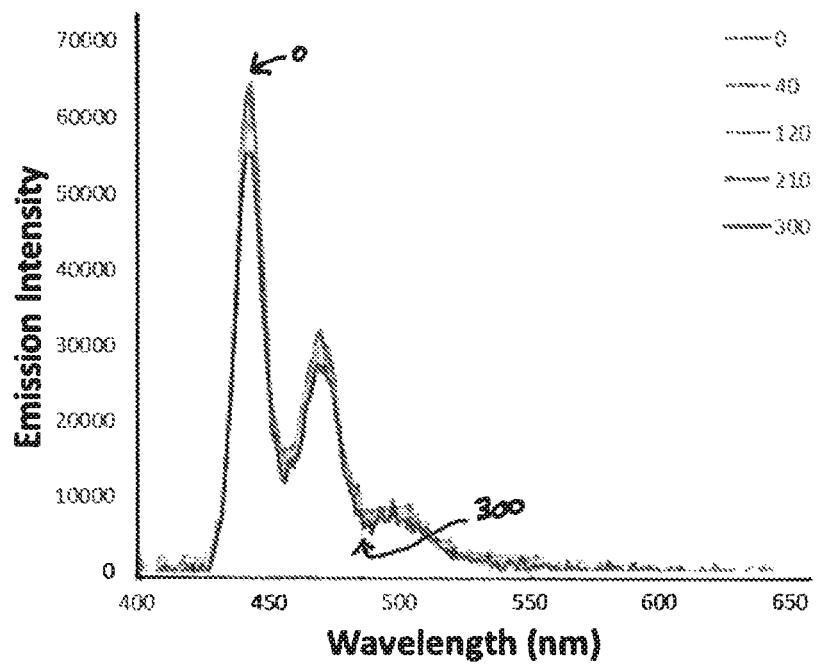
FIG. 9K shows a phosphorescent emission spectra of 6 in doped PMMA films under continuous UV irradiation (352 nm, 300 minutes).
Figure 9L:
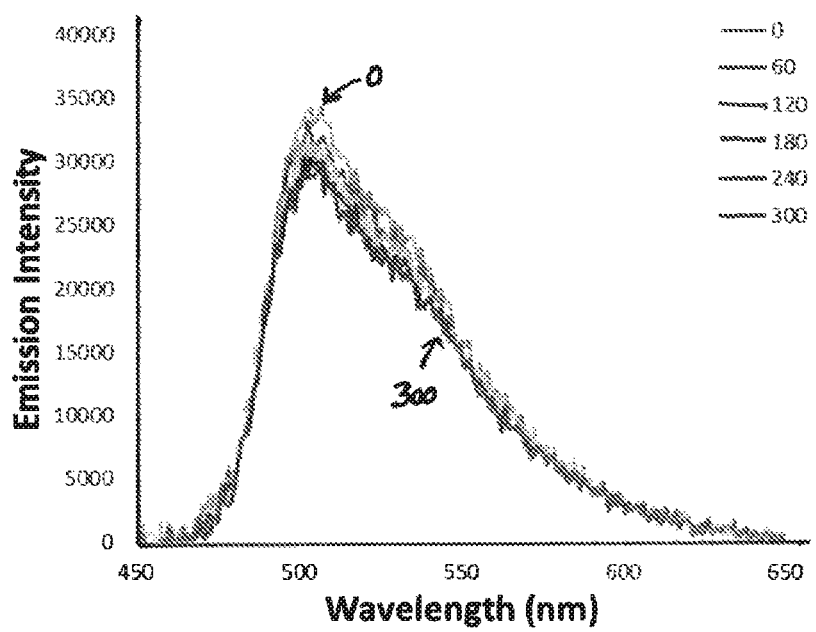
FIG. 9L shows a phosphorescent emission spectra of Ir(ppy)$_3$ in doped PMMA films under continuous UV irradiation (393 nm, 300 minutes).
Figure 9M:
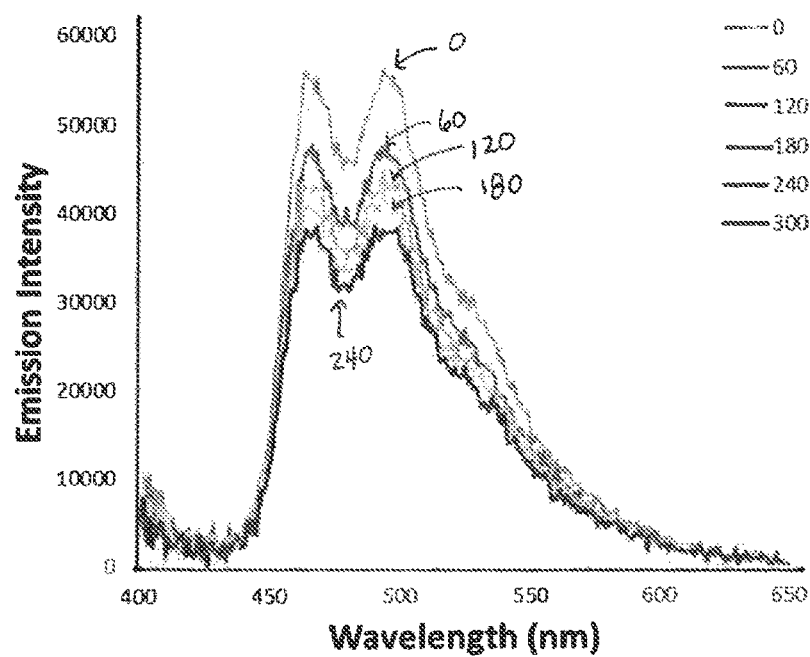
FIG. 9M shows a phosphorescent emission spectra of 8 in doped PMMA films under continuous UV irradiation (364 nm, 300 minutes).
Figure 9N:
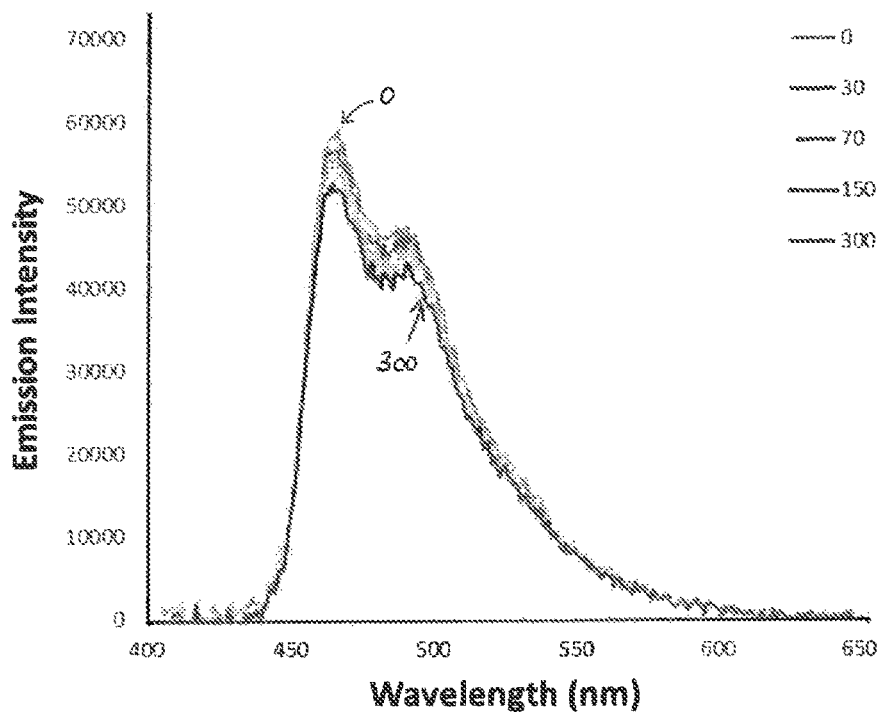
FIG. 9N shows a phosphorescent emission spectra of Firpic in doped PMMA films under continuous UV irradiation (364 nm, 300 minutes).
Figure 10:
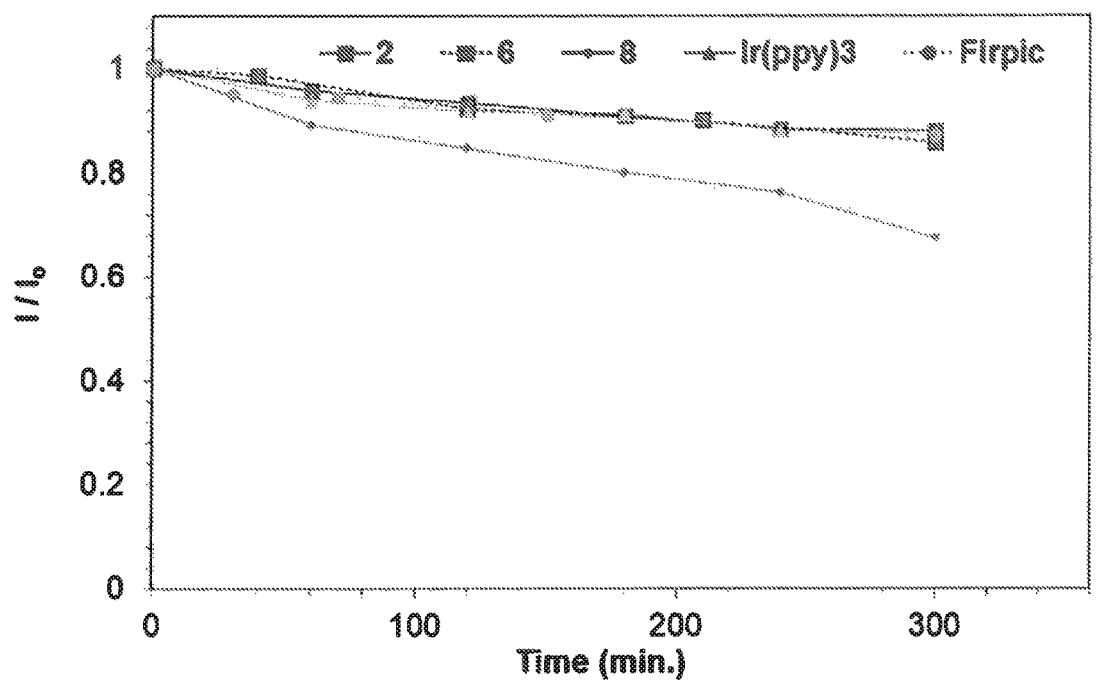
FIG. 10 shows emission intensity decay curves of the peak at $\lambda_{max}$ with time for specified compounds in 5 wt % PMMA films under continuous UV irradiation under air and at ambient temperature.

Referring to FIG. 2, an energy digram is shown for various materials used in EL devices. Referring to FIG. 3, a plot is shown of absorption and phosphorescent spectra of Pt(II) compounds in CH$_2$Cl$_2$. Referring to FIG. 4, absorption spectra are shown of 2, 6, 8, Ir(ppy)$_3$ and Firpic in CH$_2$Cl$_2$. Referring to FIG. 5A, an EL spectra is shown of an EL device based on 6. Referring to FIG. 5B, an EQE-L plot is shown for an EL device based on 6. Referring to FIGS. 6A-C, L-V curves are shown of EL devices based on 6, where FIG. 6A is 2% of 6 doped in BCPO as emitter; FIG. 6B is 5% of 6 doped in BCPO as emitter; and FIG. 6C is 10% of 6 doped in BCPO as emitter. Referring to FIGS. 7A-C, L-J-V and current efficiency and power efficiency diagrams of EL devices based on 6 are shown. Referring to FIG. 8A, a TGA diagram of 2 is shown. Referring to FIG. 8B, a TGA diagram of 6 is shown. Referring to FIGS. 9A-G, phosphorescent emission spectra are shown for specified complexes in doped PMMA films. Referring to FIG. 9H, a phosphorescent emission spectra of 4, 5 and 7 as neat powder is shown. Referring to FIG. 9I, a phosphorescent emission spectra of compounds 1-7 in 2-methyl THF at 77K is shown. Referring to FIGS. 9J to 9N, a phosphorescent emission spectra of the specified complex in doped PMMA film under continuous UV irradiation are shown. Referring to FIG. 10, a plot is shown of emission intensity over time indicating decay of the peak at $\lambda_{max}$ for 2, 6 and 8 relative to standards in 5 wt % PMMA films under continuous UV irradiation.

The following working examples further illustrate the present invention and are not intended to be limiting in any respect.

WORKING EXAMPLES

All Reactions were carried out under a nitrogen atmosphere unless otherwise noted. Reagents were purchased from Aldrich chemical company (Oakville, ON, Canada) and used as received. were performed on silica gel. $^1$H spectra were recorded on Bruker Avance 300, 400 and 500 MHz spectrometers. Thin Layer Chromatography (TLC) and flash chromatography was carried out on SiO$_2$ (silica gel F254, Whatman). Flash chromatography was carried out on silica (silica gel 60, 70-230 mesh). $^1$H and $^{13}$C spectra were recorded on a Bruker Avance 300 spectrometer () operating at 300 and 75.3 MHz respectively. Deuterated solvents were purchased from Cambridge Isotopes (St. Leonard, QC, Canada) and used without further drying. Excitation and emission spectra were obtained on a Photon Technologies International QuantaMaster Model 2 spectrometer (Anaheim, Calif., USA). Solid state quantum efficiency measurements were performed using the same spectrometer with an integration sphere. Phosphorescent decay life times were measured with an Edinburgh Instrument FLS980 spectrophotometer. Solution phosphorescence quantum yields were measured relative to 9,10-diphenylanthracene in degassed dichloromethane at 298 K. UV-Visible spectra were recorded using a Varian Carry 50 UV/Vis spectrophotometer (Varian, Inc. of Agilent Technologies, Mississauga, ON, Canada). Solution quantum yields were calculated using optically dilute solutions (A≈0.1) relative to Ir(ppy)$_3$ (T. Sajoto, P. I. Djurovich, A. B. Tamayo, J. Oxgaard, W. A. Goddard, M. E. Thompson, *J. Am. Chem. Soc.* 2009, 131, 9813-9822). Elemental analyses were performed by the University of Montreal Elemental Analysis Laboratory (Montreal, Canada). Melting points were determined on a Fisher-Johns melting point apparatus. Conveniently EL spectra may be obtained using Ocean Optics HR2000; and data involving current, voltage and luminosity may be obtained using a Keithley 238 high current source measure unit.

EL Device Fabrication: The ITO (indium-tin oxide) coated glass substrates (20 Ω/square) were first cleaned in ethanol, acetone, and soap ultrasonic bathes. All organics were thermally evaporated at a rate of 1.0 Å S$^{-1}$ at a base pressure of around 3.5×10$^{-4}$ Pa. A LiF layer (0.5 nm) was deposited at a rate of 0.2 Å S$^{-1}$. The Al electrode (cathode) was deposited at a rate of 10 Å S$^{-1}$. The active area of the diode segments was 2×2 mm$^2$. EL spectra and brightness-current density-voltage characteristics of the devices were measured by combining a Spectrascan PR-650 spectrophotometer with a computer-controlled direct-current power supply Keithley model 2400 voltage-current source under ambient condition.

Example 1

Fabrication on EL Device

Devices are fabricated in a Kurt J. Lesker LUMINOS® cluster tool with a base pressure of ~10$^{-8}$ Torr without breaking vacuum. The ITO anode is commercially patterned and coated on glass substrates 50×50 mm$^2$ with a sheet resistance less than 15 Ω/square. Substrates are ultrasonically cleaned with a standard regiment of Alconox®, acetone, and methanol followed by UV ozone treatment for 15 min. The active area for all devices is 2 mm$^2$. The film thicknesses are monitored by a calibrated quartz crystal microbalance. Current-Voltage characteristics are measured using a HP4140B picoammeter in ambient air. Luminance measurements and EL spectra are taken using a Minolta LS-110 luminance meter and an Ocean Optics USB200 spectrometer with bare fiber, respectively. The external quantum efficiency of EL devices is calculated following standard procedure. Additional details regarding device fabrication and characterization measurements have been described elsewhere (Hudson, Z. et al. J. Am. Chem. Soc. (2012) 134, 13930-13933).

Devices are fabricated by vacuum vapor deposition on ITO-coated glass substrates. Due to the wide bandgaps of these materials, care is taken to ensure that the HOMO and LUMO energy levels of both emitters were contained within the bandgap of the host material, to ensure efficient trapping of both holes and electrons. Furthermore, it is necessary to employ a host material with a sufficiently high triplet level to ensure that excitons within the device were confined to the dopant. Based on these considerations, devices are fabricated using 4,4'-N,N'-dicarbazolylbiphenyl (CBP) as the hole-transport layer, 1,3,5-tris(N-phenylbenzimidazole-2-yl)benzene (TPBI) as the electron-transport layer, and N,N'-dicarbazolyl-3,5-benzene (mCP) as host. These devices have a structure of ITO/MoO$_3$ (1 nm)/CBP (35 nm)/mCP (5 nm)/mCP:emitter (12%, 15 nm)/TPBI (65 nm)/LiF (1 nm)/Al.

Example 2

Synthesis of Ligands 3,3'-oxydianiline (see A. V. Anzalone, et al., Angew. Chem. Int. Ed, 2013, 52, 650-654), bis(3-iodophenyl)methane (see A. Avellaneda, et al., J. Org. Chem. (2012) 8:71-80), bis(3-iodophenyl)methanone (see J. R. Cox, et al., J. Am. Chem. Soc. (2013) 135:640-643), 4-(3-bromophenyl)-1-methyl-1H-1,2,3-triazole (see X. Wang, et al., Adv. Funct. Mater. (2014) 24:1911-1927) and 3-(1-hexyl-1H-1,2,3-triazol-4-yl)phenol (see C. Menendez, et al., Eur. J. Med. Chem. (2012) 52:275-283) were prepared according to literature procedures.

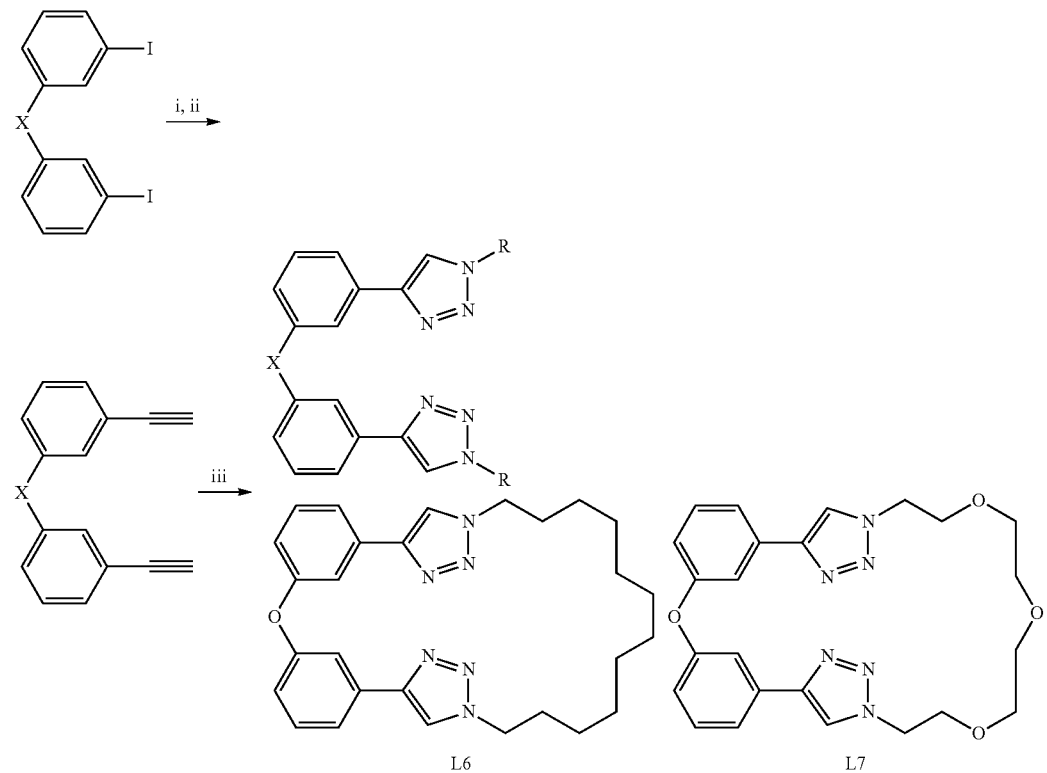

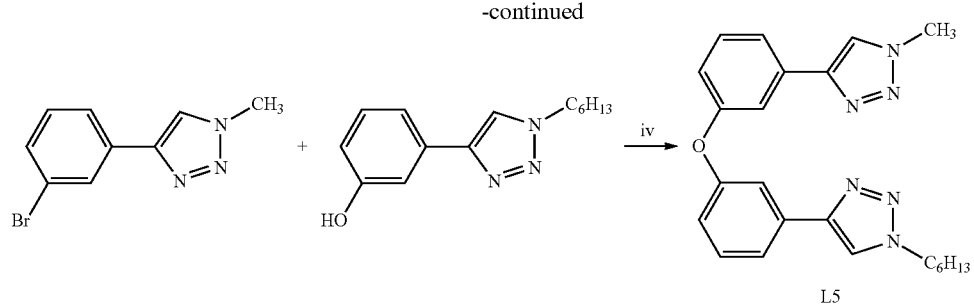

L1: X = O, R = Bn
L2: X = O, R = n-hexyl
L3: X = CH₂, R = n-hexyl
L4: X = CO, R = n-hexyl

3,3'-oxybis(iodobenzene)

In a 250 mL round bottomed flask, 3,3'-oxydianiline (4 g, 20.0 mmol) was dissolved in 100 mL of acetone. To the flask 21 mL of concentrated HCl in 30 mL of water was added dropwise. The solution was cooled to 0° C. and sodium nitrite (8.4 g, 121.8 mmol) in 50 mL of water was added slowly. The solution was stirred at 0° C. for another hour before potassium iodide (25 g, 150.6 mmol) in 50 mL water was added dropwise. The solution was stirred at 0° C. for 2 h, then at 60° C. for 4 h. Upon cooling, sodium bisulfite was added until all iodine in the solution was consumed. The mixture was then concentrated under reduced pressure. The product was dissolved in dichloromethane and washed sequentially with water and brine. The organic layer was dried over MgSO₄, filtered and the solvent was removed under reduced pressure. The solid was then purified using flash chromatography through silica using hexane as eluent to give 6.09 g 3,3'-oxybis(iodobenzene) as white powder (72% yield). ¹H NMR (300 MHz, CHLOROFORM-d) δ=7.55-7.42 (m, 2H), 7.41-7.30 (m, 2H), 7.15-7.03 (m, 2H), 7.03-6.90 (m, 2H).

3,3'-oxybis(ethynylbenzene)

A 250 mL Schlenk flask was charged with 3,3'-oxybis (iodobenzene) (5.6 g, 13.3 mmol), trimethylsilylacetylene (5.2 mL, 36.8 mmol), PdCl₂(PPh₃)₂ (0.94 g, 1.34 mmol), triphenylphosphine (0.7 g, 2.67 mmol) copper iodide (0.38 g, 2.00 mmol) and 80 mL of degassed THF/triethylamine (v:v=3:1). The mixture was stirred at room temperature overnight, and then concentrated under reduced pressure. The product was dissolved in dichloromethane and washed sequentially with saturated ammonium chloride solution, water and brine. The organic layer was dried over MgSO₄, filtered and the solvent was removed under reduced pressure. The solid was then purified using flash chromatography through silica using 10% dichloromethane in hexane as eluent. The resulting white solid was dissolved in 40 mL of tetrahydrofuran and treated with tetrabutylammonium fluoride in THF (40 mL of a 1.0 M solution). After stirring overnight, the resulting mixture was concentrated under reduced pressure. After extraction with dichloromethane, the organic layer was dried over MgSO₄, filtered and the solvent was removed under reduced pressure. The solid was then purified using flash chromatography through silica using 10% dichloromethane in hexane as eluent to afford 2.74 g 3,3'-oxybis(ethynylbenzene) as white solid (94% yield). ¹H NMR (300 MHz, CHLOROFORM-d) δ=7.39-7.23 (m, 4H), 7.13 (s, 2H), 7.03 (td, J=2.0, 7.6 Hz, 2H), 3.10 (s, 2H).

bis(3-ethynylphenyl)methanone

Prepared using the same procedure as 3,3'-oxybis(ethynylbenzene) except replacing 3,3'-oxybis(iodobenzene) with bis(3-iodophenyl)methanone (70% yield). ¹H NMR (300 MHz, CHLOROFORM-d) δ=7.91 (s, 2H), 7.76 (dd, J=7.7, 14.8 Hz, 4H), 7.56-7.42 (m, 2H), 3.15 (s, 2H).

bis(3-ethynylphenyl)methane

Prepared using the same procedure as 3,3'-oxybis(ethynylbenzene) except replacing 3,3'-oxybis(iodobenzene) with bis(3-iodophenyl)methane (88% yield). ¹H NMR (300 MHz, CHLOROFORM-d) δ=7.41-7.31 (m, 16H), 7.31-7.23 (m, 15H), 7.22-7.13 (m, 9H), 3.95 (s, 9H), 3.07 (s, 8H).

4,4'-(oxybis(3,1-phenylene))bis(1-hexyl-1H-1,2,3-triazole) (L2)

To a 50 mL Schlenk flask equipped with a magnetic stir bar was added 3,3'-oxybis(ethynylbenzene) (0.4 g, 1.83 mmol), 1-azidohexane (0.7 g, 5.78 mmol), diisopropylethylamine (0.95 g, 7.32 mmol), tris[(1-benzyl-1H-1,2,3-triazol-4-yl) methyl]amine (1 mol %) and 40 mL dichloromethane. The resulting solution was bubbled with nitrogen gas for 20 minutes. [Cu(CH₃CN)₄]PF₆ (1 mol %) was added as a catalyst. The resulting mixture was stirred overnight, after which the solvent was removed under reduced pressure. The crude product was dissolved in dichloromethane and washed with saturated ammonium chloride solution, water and brine. The organic layer was dried over MgSO₄, filtered and the solvent was removed under reduced pressure. The product was then purified using flash chromatography through silica (8:1 dichloromethane: ethyl acetate as eluent) to afford 0.48 g 4,4'-(oxybis(3,1-phenylene))bis (1-hexyl-1H-1,2,3-triazole) as white solid (57% yield). ¹H NMR (300 MHz, CHLOROFORM-d) δ=7.73 (s, 2H), 7.64 (d, J=7.7 Hz, 2H), 7.52 (t, J=1.9 Hz, 2H), 7.42 (t, J=7.9 Hz, 2H), 7.03 (dd, J=1.5, 8.1 Hz, 2H), 4.40 (t, J=7.3 Hz, 4H), 1.94 (d, J=7.2 Hz, 4H), 1.34 (br. s., 12H), 0.98-0.81 (m, 6H).

4,4'-(oxybis(3,1-phenylene))bis(1-benzyl-1H-1,2,3-triazole) (L1)

Prepared using the same procedure as L2 except replacing 1-azidohexane with benzyl azide (62% yield). ¹H NMR (300

MHz, CHLOROFORM-d) δ=7.73-7.52 (m, 4H), 7.51-7.32 (m, 12H), 6.99 (d, J=6.6 Hz, 2H), 5.58 (s, 4H).

bis(3-(1-hexyl-1H-1,2,3-triazol-4-yl)phenyl)methane (L3)

Prepared using the same procedure as L2 except replacing (3,3'-oxybis(ethynylbenzene) with bis(3-ethynylphenyl)methane (53% yield). $^1$H NMR (300 MHz, CHLOROFORM-d) δ=7.80 (s, 2H), 7.76 (br. s., 2H), 7.69 (d, J=7.0 Hz, 2H), 7.39 (t, J=7.6 Hz, 2H), 7.24 (d, J=7.7 Hz, 2H), 4.39 (t, J=7.3 Hz, 4H), 4.12 (s, 2H), 1.95 (br. s., 4H), 1.36 (br. s., 12H), 0.92 (br. s., 5H).

bis(3-(1-hexyl-1H-1,2,3-triazol-4-yl)phenyl)methanone (L4)

Prepared using the same procedure as L2 except replacing (3,3'-oxybis(ethynylbenzene) with bis(3-ethynylphenyl)methanone (74% yield). $^1$H NMR (300 MHz, CHLOROFORM-d) δ=8.28-8.14 (m, 4H), 7.85 (s, 2H), 7.79 (d, J=7.6 Hz, 2H), 7.66-7.50 (m, 2H), 4.43 (t, J=7.2 Hz, 4H), 1.96 (d, J=6.9 Hz, 4H), 1.36 (br. s., 12H), 1.01-0.79 (m, 6H).

($1^4Z,5^4Z$)-$1^1$H,$5^1$H-3-oxa-1,5(4,1)-ditriazola-2,4(1,3)-dibenzenacycloheptadecaphane (L6)

To a 500 mL Schlenk flask equipped with a magnetic stir bar was added 3,3'-oxybis(ethynylbenzene) (0.4 g, 1.83 mmol), 1,12-diazidododecane (0.49 g, 1.92 mmol), diisopropylethylamine (0.95 g, 7.32 mmol), tris[(1-benzyl-1H-1,2,3-triazol-4-yl)methyl]amine (1 mol %) and 240 mL of dichloromethane. The resulting solution was bubbled with nitrogen gas for 30 minutes. [Cu(CH$_3$CN)$_4$]PF$_6$ (1 mol %) was added as a catalyst. The resulting mixture was stirred at room temperature for 6 days, after which the solvent was removed under reduced pressure. The crude product was dissolved in dichloromethane and washed with saturated ammonium chloride solution, water and brine. The organic layer was dried over MgSO$_4$, filtered and the solvent was removed under reduced pressure. The product was then purified using flash chromatography through silica (5:1 dichloromethane:ethyl acetate as eluent) to afford 0.2 g ($1^4Z,5^4Z$)-$1^1$H,$5^1$H-3-oxa-1,5(4,1)-ditriazola-2,4(1,3)-dibenzenacycloheptadecaphane as white solid (24% yield). $^1$H NMR (300 MHz, CHLOROFORM-d) δ=7.74-7.60 (m, 4H), 7.48 (t, J=7.8 Hz, 2H), 7.33 (s, 2H), 7.19 (d, J=8.1 Hz, 2H), 4.39 (t, J=6.5 Hz, 4H), 1.88 (br. s., 4H), 1.35-1.05 (m, 16H).

($1^4Z,5^4Z$)-$1^1$H,$5^1$H-3,8,11,14-tetraoxa-1,5(4,1)-ditriazola-2,4(1,3)-dibenzenacyclohexadecaphane (L7)

Prepared using the same procedure as L6 except replacing 1,12-diazidododecane with Tetraethylene glycol bisazide (17% yield). $^1$H NMR (300 MHz, CHLOROFORM-d) δ=7.84-7.72 (m, 4H), 7.50 (t, J=7.9 Hz, 2H), 7.25-7.11 (m, 4H), 4.55 (t, J=5.3 Hz, 4H), 385 (t, J=5.3 Hz, 4H), 3.48 (t, J=5.3 Hz, 4H), 3.41 (t, J=5.3 Hz, 4H).

1-hexyl-4-(3-(3-(1-methyl-1H-1,2,3-triazol-4-yl)phenoxy)phenyl)-1H-1,2,3-triazole (L5)

A 100 mL three-necked round bottomed flask, equipped with a magnetic stir bar and a condenser, was charged with 4-(3-bromophenyl)-1-methyl-1H-1,2,3-triazole (0.4 g, 1.68 mmol), 3-(1-hexyl-1H-1,2,3-triazol-4-yl) phenol (0.45 g, 1.84 mmol), K$_3$PO$_4$ (0.71 g, 3.36 mmol), copper iodide (0.032 g, 0.17 mmol), 2-picolinic acid (0.041 g, 0.34 mmol) and 50 mL of degassed DMSO. The mixture was stirred at 90° C. for 4 days before 75 mL of water was added. The mixture extracted with ethyl acetate and then washed sequentially with saturated ammonium chloride solution, water and brine. The organic layer was dried over MgSO$_4$, filtered and the solvent was removed under reduced pressure. The solid was then purified using flash chromatography through silica(8:1 dichloromethane:ethyl acetate as eluent) to afford 0.52 g 1-hexyl-4-(3-(3-(1-methyl-1H-1,2,3-triazol-4-yl)phenoxy)phenyl)-1H-1,2,3-triazole as white solid (77% yield). $^1$H NMR (300 MHz, CHLOROFORM-d) δ=7.74-7.72 (m, 2H), 7.67-7.57 (m, 2H), 7.55-7.47 (m, 2H), 7.40 (t, J=7.9 Hz, 2H), 7.02 (dd, J=1.7, 8.1 Hz, 2H), 4.38 (t, J=7.2 Hz, 2H), 4.13 (s, 3H), 1.93 (d, J=7.0 Hz, 2H), 1.45-1.20 (m, 6H), 0.98-0.79 (m, 3H).

Figure 11:
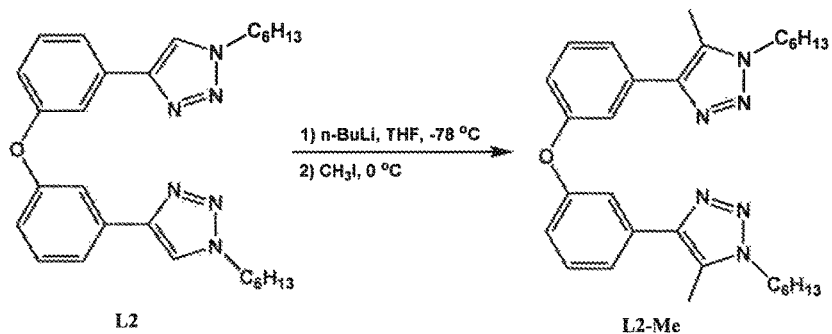
FIG. 11 shows a reaction scheme describing the formation of ligand L2-Me as discussed in Example 2.

L2-Me:See FIG. 11 for reaction scheme. To a 100 mL Schlenk flask with a stir bar was added L2 (0.4 g) and 20 mL of dry THF. The resulting solution was stirred at −78° C. for 30 minutes. 1.2 mL of 2.5 M n-Butyllithium (3.00 mmol) was then slowly added. The mixture was maintained at −78° C. for 10 mins, and methyl iodide (0.5 mL) was added. The resulting mixture was stirred at −78° C. for one hour. It was then slowly warmed up to 0° C. and stirred for two hours. Solvent was removed under reduced pressure. Crude product was extracted with dichloromethane, and washed with water and brine. Combined organic phases were dried over MgSO$_4$, filtered, and purified using flash chromatography on silica to afford 0.3 g L2-Me as a white solid.

L2-Me: Yield 71%. $^1$H NMR (300 MHz, CDCl3, δ): 7.53-7.35 (m, 6H), 7.03 (dt, J=7.8, 1.4 Hz, 2H), 4.29 (t, J=7.3 Hz, 4H), 2.45 (s, 6H), 1.97-1.83 (m, 4H), 1.35 (br. s., 12H), 0.96-0.84 (m, 6H).

Example 3

Syntheses of Pt(II) Compounds

The general synthetic procedures for the Pt(II) compounds are provided below. The Pt(II) compounds have the tendency to co-crystallize with solvent molecules such as THF and CH$_2$Cl$_2$. For some of the compounds, the solvent molecules were positively identified in the crystal lattice of the Pt(II) compounds.

General Procedure for the Synthesis of Pt(II) Compounds

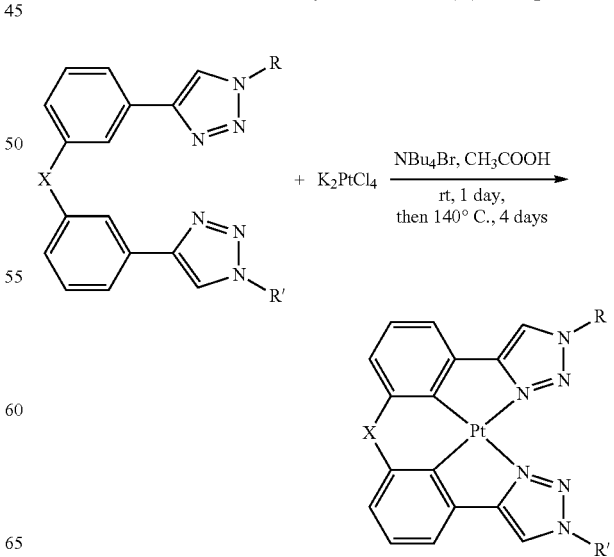

The ligand (0.08 g), tetrabutylammonium bromide (0.006 g) and K$_2$PtCl$_4$ (0.08 g) were added to a sealed tube with 10 mL dry degassed acetic acid. The mixture was stirred at room temperature for 1 day, and then heated at 140° C. for 4 days. 10 mL of water was added to the resulting solution and the precipitate was collected via vacuum filtration. The solid was then dissolved in dichloromethane and washed with water and brine. The combined organic phase was dried over MgSO$_4$, filtered and purified on using flash chromatography through silica (dichloromethane as eluent).

1: Yield 15%. $^1$H NMR (400 MHz, Dichloromethane-d$_2$) δ=7.68 (s, 2H), 7.50-7.35 (m, 8 H), 7.24-7.05 (m, 8 H), 5.68 (s, 4 H). HRMS (ESI) calculated for C30H23N6OPt [M+H]$^+$: calcd. 678.1576, found 678.1575.

2: Yield 23%. $^1$H NMR (400 MHz, Dichloromethane-d$_2$): δ=7.76 (s, 2 H), 7.29-7.24 (m, 2 H), 7.24-7.18 (m, 2 H), 7.10 (d, J=8.1 Hz, 2 H), 4.47 (t, J=7.3 Hz, 4 H), 2.10-1.98 (m, 4 H), 1.49-1.29 (m, 12 H), 0.91 ppm (t, J=6.9 Hz, 6 H). HRMS (ESI) calculated for C28H35N6OPt [M+H]$^+$: calcd. 666.2515, found 666.2533.

3: Yield 14%. $^1$H NMR (400 MHz, Dichloromethane-d$_2$) δ=7.76 (d, J=1.5 Hz, 2 H), 7.37 (d, J=7.3 Hz, 2 H), 7.29-7.09 (m, 4 H), 4.91 (s, 2 H), 4.50 (t, J=7.4 Hz, 4 H), 2.07 (quin, J=7.1 Hz, 4 H), 1.53-1.30 (m, 12 H), 0.95 (t, J=6.2 Hz, 6 H). HRMS (ESI) calculated for C29H37N6Pt [M+H]$^+$: calcd. 664.2722, found 664.2681.

4: Yield 14%. $^1$H NMR (400 MHz, Dichloromethane-d$_2$) δ=8.21 (dd, J=1.3, 8.1 Hz, 2 H), 7.80 (s, 2 H), 7.61 (dd, J=1.4, 7.2 Hz, 2 H), 7.27 (t, J=7.7 Hz, 2 H), 4.50 (t, J=7.4 Hz, 4 H), 2.05 (t, J=7.6 Hz, 4 H), 1.50-1.24 (m, 12 H), 0.98-0.83 (m, 6 H). HRMS (ESI) calculated for C29H35N6OPt [M+H]$^+$: calcd. 678.2515, found 678.2513.

5: Yield 22%. $^1$H NMR (500 MHz, Dichloromethane-d$_2$): δ=7.77 (s, 1 H), 7.76 (s, 1H), 7.30-7.05 (m, 6 H), 4.48 (t, J=7.3 Hz, 2 H), 4.22 (s, 3 H), 2.09-1.98 (m, 2 H), 1.46-1.30 (m, 6H), 0.92 ppm (m, 3 H). HRMS (ESI) calculated for C23H25N6OPt [M+H]$^+$: calcd. 596.1732, found 596.1730.

6: Yield 52%. $^1$H NMR (400 MHz, Dichloromethane-d$_2$): δ=7.74 (s, 2 H), 7.30-7.23 (m, 2 H), 7.23-7.17 (m, 2 H), 7.15 (s, 2 H), 4.51 (t, J=6.4 Hz, 4 H), 2.12-1.98 (m, 4 H), 1.50-1.23 ppm (m, 16 H). HRMS (ESI) calculated for C28H33N6OPt [M+H]$^+$: calcd. 664.2358, found 664.2333.

7: Yield 11%. $^1$H NMR (400 MHz, Dichloromethane-d$_2$): δ=7.73 (s, 2 H), 7.30-7.24 (m, 2 H), 7.24-7.18 (m, 2 H), 7.18-7.03 (m, 2 H), 4.70-4.60 (m, 4 H), 3.98-3.91 (m, 4 H), 3.64 ppm (s, 8 H). HRMS (ESI) calculated for C$_{24}$H$_{25}$N$_6$O$_4$Pt [M+H]$^+$: calcd. 656.1580, found 656.1592.

Figure 12:
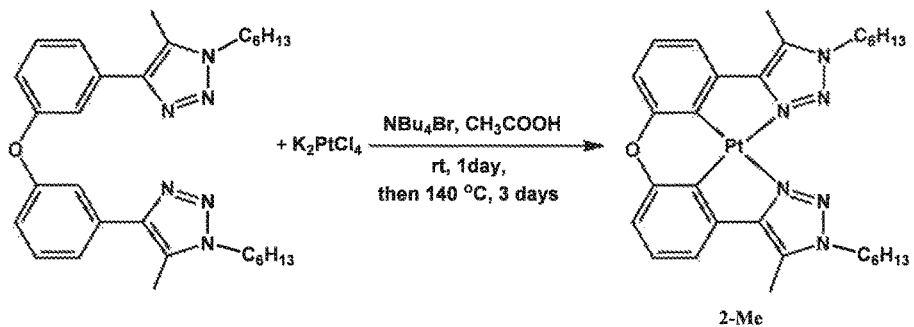
FIG. 12 shows a reaction scheme describing the formation of complex 2-Me as discussed in Example 3.
Figure 13:
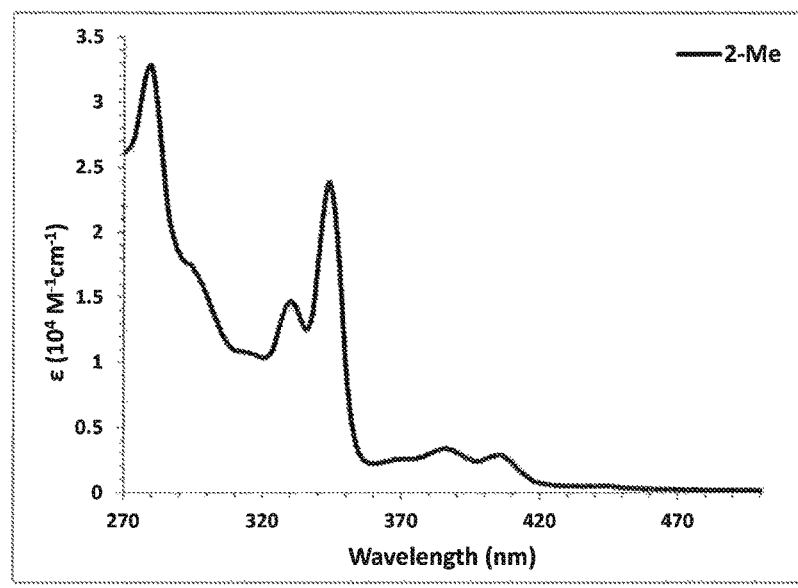
FIG. 13 shows a UV-vis spectrum of 2-Me in $CH_2Cl_2$ ($2 \times 10^{-5}$ M) at ambient temperature.
Figure 14:
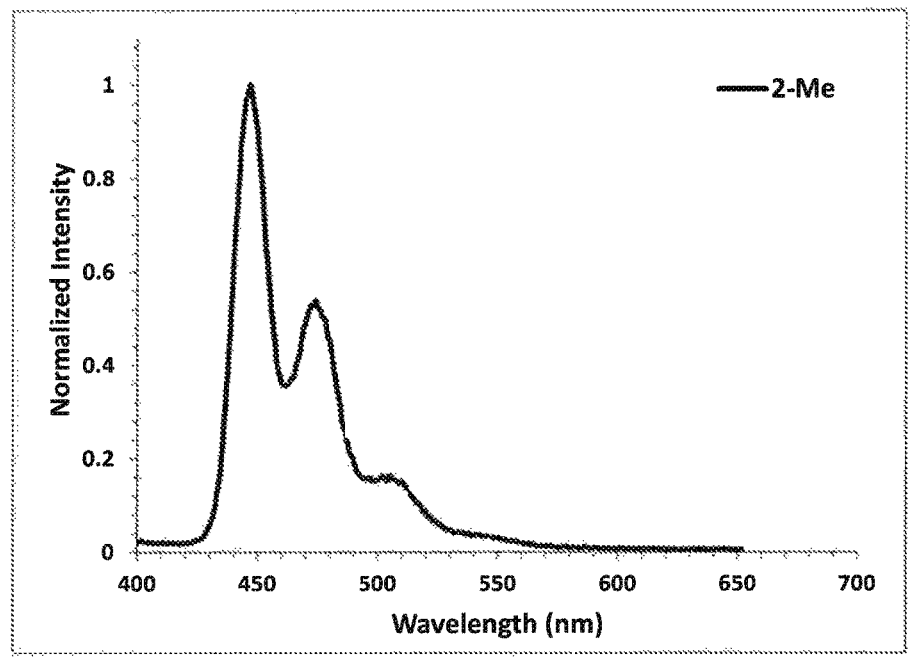
FIG. 14 shows a phosphorescent spectra of 2-Me in $CH_2Cl_2$ at ambient temperature.
Figure 15:
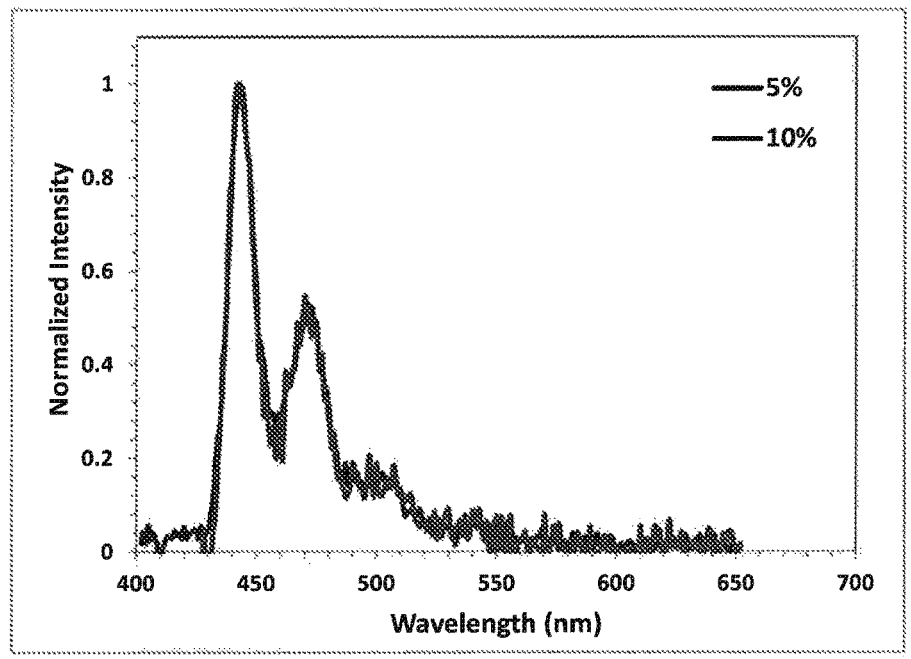
FIG. 15 shows a phosphorescent emission spectra of 2-Me at 5% or 10% as indicated, in doped PMMA films.

2-Me: See FIG. 12 for a reaction scheme, and FIGS. 13-15 for relevant spectra. Yield 44%. $^1$H NMR (400 MHz, CD$_2$Cl$_2$, δ=7.27 (d, J=7.7 Hz, 2 H), 7.21 (t, J=7.7 Hz, 2 H), 7.09 (d, J=7.7 Hz, 2 H), 4.38 (t, J=7.6 Hz, 4 H), 2.63 (s, 6H), 2.00-1.90 (m, 4 H), 1.49-1.29 (m, 12 H), 0.90 ppm (t, J=6.9 Hz, 6 H).

All scientific and patent publications cited herein are hereby incorporated in their entirety by reference. Although this invention is described in detail with reference to embodiments thereof, these embodiments are offered to illustrate but not to limit the invention. It is possible to make other embodiments that employ the principles of the invention and that fall within its spirit and scope as defined by the claims appended hereto.

TABLE 1

| Structural Formula Structure and nickname | |
| --- | --- |
| [structure with Bn groups] | L1 |
| [structure with C$_6$H$_{13}$ groups, ether linkage] | L2 |
| [structure with C$_6$H$_{13}$ groups, CH$_2$ linkage] | L3 |
| [structure with C$_6$H$_{13}$ groups, C=O linkage] | L4 |
| [structure with CH$_3$ and C$_6$H$_{13}$ groups] | L5 |
| [macrocyclic structure] | L6 |

TABLE 1-continued

Structural Formula
Structure and nickname

TABLE 1-continued
Structural Formula
Structure and nickname
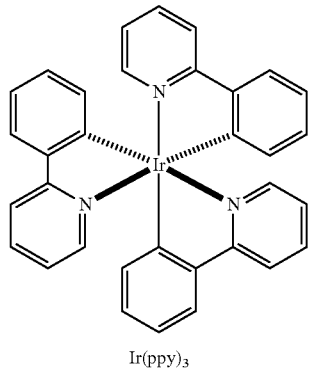
Ir(ppy)₃
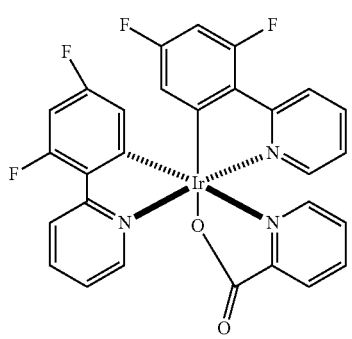
Firpic
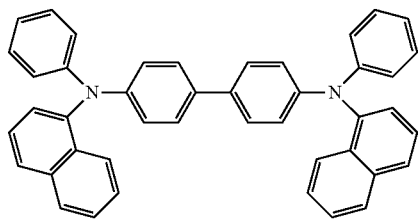 [SMILES: c1ccc(N(c2ccc(-c3ccc(N(c4ccccc4)c4cccc5ccccc45)cc3)cc2)c2cccc3ccccc23)cc1]
NPB
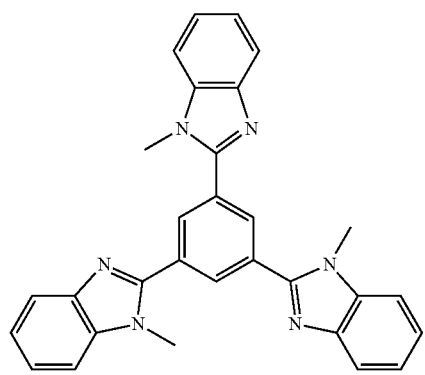 [SMILES: Cn1c(-c2cc(-c3nc4ccccc4n3C)cc(-c3nc4ccccc4n3C)c2)nc2ccccc21]
TPBi
TABLE 1-continued
Structural Formula
Structure and nickname
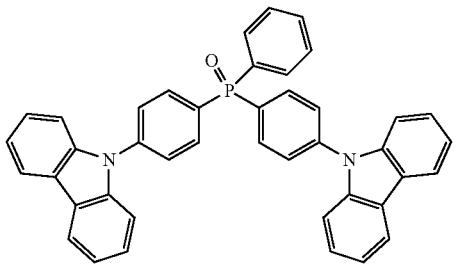 [SMILES: O=P(c1ccccc1)(c1ccc(-n2c3ccccc3c3ccccc32)cc1)c1ccc(-n2c3ccccc3c3ccccc32)cc1]
BCPO
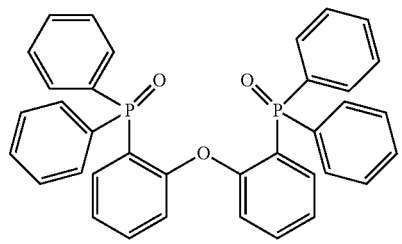 [SMILES: O=P(c1ccccc1)(c1ccccc1)c1ccccc1Oc1ccccc1P(=O)(c1ccccc1)c1ccccc1]
DPEPO
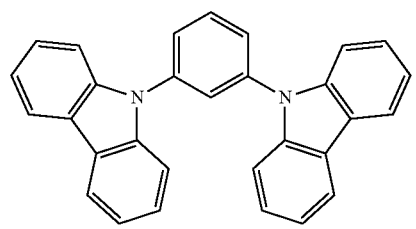 [SMILES: c1cc(-n2c3ccccc3c3ccccc32)cc(-n2c3ccccc3c3ccccc32)c1]
mCP
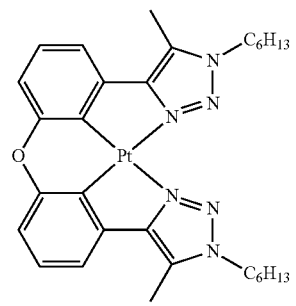
2-Me

TABLE 2

Photophysical Properties

| | | Emission 298K | | | | | | Emission 77K[c] | |
|---|---|---|---|---|---|---|---|---|---|
| | | $\lambda_{max}$ [nm] | | | $\phi_{PL}$[b] | | | | |
| | $\lambda_{max}$ [nm] | | 5% | 10% | | 5% | 10% | | |
| | $\varepsilon$ [$10^4$ cm$^{-1}$M$^{-1}$][a] | CH$_2$Cl$_2$ | PMMA | PMMA | CH$_2$Cl$_2$ | PMMA | PMMA | $\lambda_{max}$ [nm] | T$_P$ [μs] |
| 1 | 331 (1.41), 344 (2.35), 387 (0.29) | 450 | 447 | 448 | 0.39 | 0.46 | 0.27 | 443 | 4.1 (58%), 9.5 (42%) |
| 2 | 333 (1.40), 344 (2.35), 386 (0.29) | 450 | 447 | 448 | 0.46 | 0.97 | 0.62 | 443 | 4.5 (63%), 9.7 (37%) |
| 3 | 323 (0.77), 349 (1.84) | 445 | 442 | 443 | 0.14 | 0.38 | 0.15 | 439 | 5.0 (48%), 9.3 (52%) |
| 4 | 316 (1.10), 347 (1.00), 404 (0.68) | 477 | 467 | 470 | 0.18 | 0.50 | 0.16 | 457 | 15.0 (100%) |
| 5 | 331 (1.15), 344 (1.91), 386 (0.26) | 449 | 446 | 446 | 0.57 | 0.60 | 0.69 | 443 | 4.6 (62%), 9.7 (38%) |
| 6 | 335 (1.28), 344 (2.23), 390 (0.24) | 448 | 447 | 447 | 0.58 | 0.83 | 0.95 | 442 | 4.6 (63%), 9.9 (37%) |
| 7 | 331 (1.05), 344 (1.82), 386 (0.21) | 449 | 446 | 446 | 0.62 | 0.84 | 0.48 | 443 | 4.7 (63%), 9.7 (37%) |

[a]Measured in CH$_2$Cl$_2$ at $2 \times 10^{-5}$M.
[b]The solution quantum efficiency was determined in CH$_2$Cl$_2$ using 9,10-diphenylanthracene as the reference under nitrogen. The solid state quantum efficiency was measured using an integration sphere. All quantum yields are ±10%.
[c]Recorded in 2-Methyl THF (~$2.0 \times 10^{-5}$M)

TABLE 3

EL device data for 6

| Device | EL $\lambda_{max}$ (nm)[a] | $V_{on}$ (V)[b] | L (cd/m$^2$, V)[c] | $\eta_{ext}$ (%)[d] 10 cd/m$^2$ | 100 cd/m$^2$ | 1000 cd/m$^2$ | $\eta_c$ (cd/A)[e] | $\eta_p$ (lm/W)[e] | CIE (x, y)[a] |
|---|---|---|---|---|---|---|---|---|---|
| 2% 6 | 452 | 3.2 | 6342, 10.0 | 6.9 | 6.0 | 4.8 | 7.1 | 7.0 | (0.11, 0.14) |
| 5% 6 | 452 | 3.2 | 8798, 11.5 | 7.2 | 6.5 | 5.4 | 8.4 | 8.2 | (0.14, 0.13) |
| 10% 6 | 452 | 3.2 | 10676, 12.5 | 9.5 | 9.1 | 7.6 | 11.0 | 10.8 | (0.14, 0.14) |

[a]Value taken at L = 5000 cd/m$^2$.
[b]The applied voltage ($V_{on}$) is defined as brightness of 1 cd/m$^2$.
[c]The luminance (L) is the maximum value.
[d]External quantum efficiency (EQE, $\eta_{ext}$).
[e]Current efficiency ($\eta_c$) and power efficiency ($\eta_p$) are the maximum values.

TABLE 4

Photophysical data of 2-Me

| | Absorption[a] | Emission, $\lambda_{max}$ [nm], 298K | | | | | |
|---|---|---|---|---|---|---|---|
| | $\lambda_{max}$ [nm] $\varepsilon$ | $\lambda_{max}$ [nm] | | | $\phi_{PL}$[b] | | |
| Compd | [$10^4$ cm$^{-1}$M$^{-1}$] | CH$_2$Cl$_2$ | PMMA (wt %) 5% | 10% | CH$_2$Cl$_2$ | PMMA (wt %) 5% | 10% |
| 2-Me | 330 (1.47), 344 (2.38), 384 (0.34), 406 (0.29) | 447 | 444 | 444 | 0.12 | 0.15 | 0.03 |

[a]Measured in CH$_2$Cl$_2$ at $2 \times 10^{-5}$M.
[b]The solution quantum efficiency was determined in CH$_2$Cl$_2$ using 9,10-diphenylanthracene as the reference under nitrogen. The solid state quantum efficiency was measured using an integration sphere. All quantum yields have an estimated error of ~10%.

We claim:

1. A compound having general formula (1):

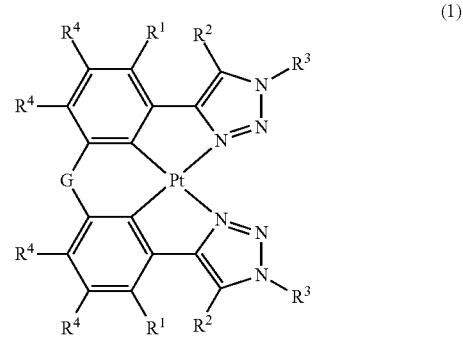

wherein G is oxygen, aliphatic, methylene, carbonyl, amine, silylene, phosphine, phosphine oxide, sulfur, sulfonyl, or a combination thereof;

R¹ and R² are independently a hydrogen, an aliphatic moiety, or fluorine, with the proviso that if one of R¹ and R² is aliphatic, CF₃, or fluoro, then the other is hydrogen;

R³ is independently H, or a substituted or unsubstituted aliphatic moiety, substituted or unsubstituted aryl moiety, a substituted or unsubstituted amine, halo, thioether, ether, or any combination thereof, and the R³ of one triazolyl ring can be joined to the R³ of the other triazolyl ring; and R⁴ is optionally further substituted, and is a non-aromatic carbocycle or heterocycle, an aryl group (which includes a heteroaryl) that is attached as a fused ring or as a substituent, a hydroxy group, nitro, amino, halo, BR₂, B(aryl)₂, aryl-B(aryl)₂, NR₂, OR, a nitrile group, —C(halo)₃, and R, where R is a substituted or unsubstituted aliphatic group having 1-24 carbon atoms which may be straight, branched or cyclic H, a substituted or unsubstituted aliphatic moiety, halo, a substituted or unsubstituted aryl moiety, or any combination thereof.

2. The compound of claim 1, wherein the compound of general formula (1) is:

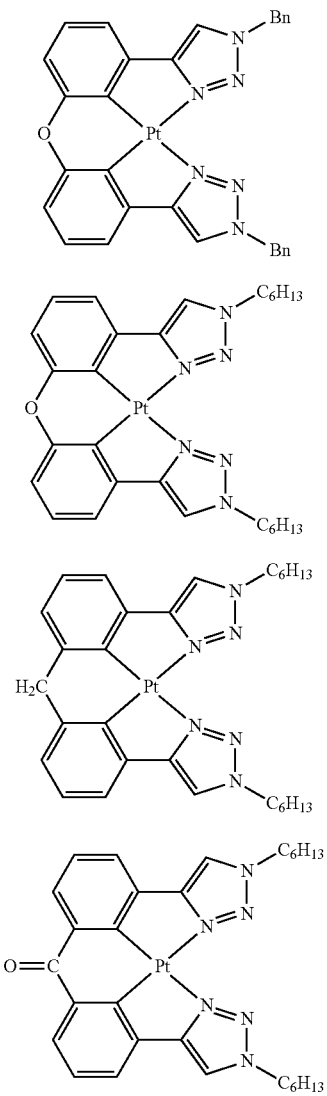

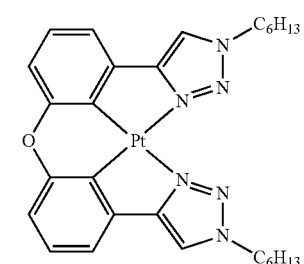

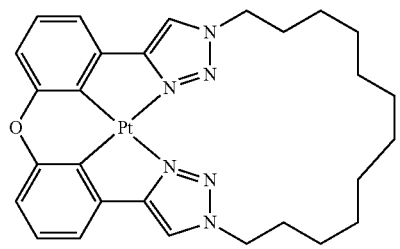

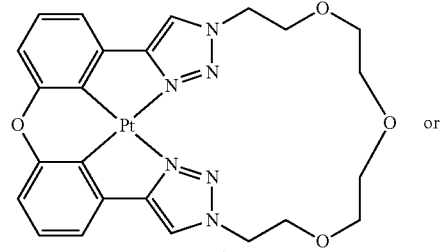

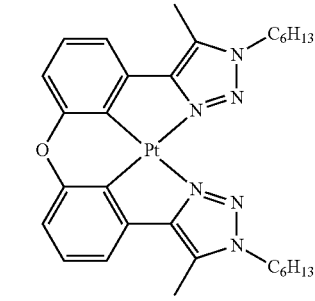

wherein Bn is benzyl.

3. A compound as claimed in claim 1, wherein the compound is photoluminescent or electroluminescent.

4. A composition comprising a photoluminescent or electroluminescent compound as claimed in claim 3, an organic polymer, and a solvent.

5. A photoluminescent product or an electroluminescent product comprising a compound as claimed in claim 3.

6. The product of claim 5, which is a display device or a lighting device.

7. A method of producing electroluminescence, comprising the steps of:
providing an electroluminescent compound as claimed in claim 3, and applying a voltage across said compound so that said compound electroluminesces.

8. An electroluminescent device for use with an applied voltage, comprising:
a first electrode,
an emitter which is an electroluminescent compound as claimed in claim 3 optionally in a host layer, and
a second, transparent electrode, wherein voltage is applied to the two electrodes to produce an electric field across the emitter so that the emitter electroluminesces.

9. An electroluminescent device for use with an applied voltage, comprising:
a first electrode,
a second, transparent electrode,
an electron transport layer adjacent the first electrode,
a hole transport layer adjacent the second electrode, and
an emitter which is an electroluminescent compound as claimed in claim 3 optionally in a host layer, interposed between the electron transport layer and the hole transport layer,
wherein voltage is applied to the two electrodes to produce an electric field across the emitter so that the emitter electroluminesces.

10. The device of claim 9, wherein the emissive layer further comprises a host.

11. An electroluminescent device for use with an applied voltage, comprising:
a first electrode,
an emitter which is an electroluminescent compound as claimed in claim 3, and
a second, transparent electrode,
wherein voltage is applied to the two electrodes to produce an electric field across the emitter so that the emitter electroluminesces.

12. An electroluminescent device for use with an applied voltage, comprising:
a first electrode,
a second, transparent electrode,
an electron transport layer adjacent the first electrode,
a hole transport layer adjacent the second electrode, and
an emitter which is an electroluminescent compound as claimed in claim 3 interposed between the electron transport layer and the hole transport layer,
wherein voltage is applied to the two electrodes to produce an electric field across the emitter so that the emitter electroluminesces.

13. An electroluminescent device for use with an applied voltage, comprising:
a first electrode,
a second, transparent electrode,
a layer which is both an emitter and an electron transporter which is an electroluminescent compound as claimed in claim 3 and which is located adjacent the first electrode, and
a hole transport layer which is interposed between the emitter and electron transport layer and the second electrode,
wherein voltage is applied to the two electrodes to produce an electric field so that the emitter electroluminesces.

14. An electroluminescent device for use with an applied voltage, comprising:
a first electrode,
a second, transparent electrode,
a layer which is all of an emitter, an electron transporter and a hole transporter which is an electroluminescent compound as claimed in claim 3 and which is interposed between the first and the second electrode,
wherein voltage is applied to the two electrodes to produce an electric field so that the emitter electroluminesces.

15. A light emitting device comprising:
an anode;
a cathode; and
an emissive layer, disposed between the anode and the cathode, wherein the emissive layer comprises a compound of general formula (1) of claim 1.

16. A consumer product comprising the device of claim 15.

17. An electroluminescent device for use with an applied voltage, comprising:
a first electrode,
a second, transparent electrode,
an electron transport layer which is a compound as claimed in claim 1 and which is located adjacent the first electrode,
a hole transport layer adjacent the second electrode, and
an emitter which is interposed between the electron transport layer and the hole transport layer,
wherein voltage is applied to the two electrodes to produce an electric field so that the emitter electroluminesces.

18. An electroluminescent device for use with an applied voltage, comprising:
a first electrode,
a second, transparent electrode,
an electron transport layer which is located adjacent the first electrode,
a hole transport layer which is a compound as claimed in claim 1 and which is located adjacent the second electrode, and
an emitter which is interposed between the electron transport layer and the hole transport layer,
wherein voltage is applied to the two electrodes to produce an electric field so that the emitter electroluminesces.

19. An electroluminescent device for use with an applied voltage, comprising:
a first electrode,
a second, transparent electrode,
a layer which is both an electron transporter and an emitter which is located adjacent the first electrode, and
a hole transport layer which is a compound as claimed in claim 1 and which is interposed between the electron transport layer and the second electrode,
wherein voltage is applied to the two electrodes to produce an electric field so that the emitter electroluminesces.

20. An electroluminescent device for use with an applied voltage, comprising:
a first electrode,
a second, transparent electrode,
an electron transport layer which is located adjacent the first electrode, and
a layer which is both an emitter and a hole transporter which is a compound as claimed in claim 1 and which is interposed between the electron transport layer and the second electrode,
wherein voltage is applied to the two electrodes to produce an electric field so that the emitter electroluminesces.

* * * * *